United States Patent [19]
Abrahamson et al.

[11] Patent Number: 5,769,821
[45] Date of Patent: Jun. 23, 1998

[54] CATHETER TIP RETAINER

[75] Inventors: Timothy A. Abrahamson; Pauline R. Young, both of Seattle; Margo L. Gisselberg, Lynnwood, all of Wash.

[73] Assignee: Quinton Instrument Company, Bothell, Wash.

[21] Appl. No.: 825,436

[22] Filed: Mar. 28, 1997

Related U.S. Application Data

[63] Continuation of Ser. No. 302,152, Sep. 8, 1994, abandoned, which is a continuation of Ser. No. 137,628, Oct. 15, 1993, abandoned, which is a continuation-in-part of Ser. No. 844,715, Mar. 2, 1992, abandoned.

[51] Int. Cl.$^6$ ................................................. A61M 29/00
[52] U.S. Cl. .......................... 604/104; 604/108; 606/198
[58] Field of Search .................................. 604/104–107, 604/160, 174, 175, 108; 606/198–200, 108, 191

[56] References Cited

U.S. PATENT DOCUMENTS

| | | |
|---|---|---|
| 2,701,559 | 2/1955 | Cooper . |
| 3,108,595 | 10/1963 | Overment . |
| 4,425,908 | 1/1984 | Simon ..................................... 128/1 R |
| 4,434,797 | 3/1984 | Silander .................................. 128/343 |
| 4,643,184 | 2/1987 | Mobin-Uddin ...................... 128/303 R |
| 4,654,028 | 3/1987 | Suma ....................................... 604/106 |
| 4,733,669 | 3/1988 | Segal ....................................... 128/663 |
| 4,808,882 | 2/1989 | Parker et al. ........................... 313/625 |
| 4,813,930 | 3/1989 | Elliott ....................................... 604/53 |
| 4,909,789 | 3/1990 | Taguchi et al. ......................... 604/107 |
| 4,921,484 | 5/1990 | Hillstead ................................ 604/104 |
| 4,936,823 | 6/1990 | Colvin et al. .............................. 600/7 |
| 4,944,745 | 7/1990 | Sogard et al. .......................... 606/194 |
| 4,957,484 | 9/1990 | Murtfeldt ................................. 604/53 |
| 5,041,093 | 8/1991 | Chu ......................................... 604/104 |
| 5,098,440 | 3/1992 | Hillstead ................................ 606/108 |
| 5,122,125 | 6/1992 | Deuss ..................................... 604/282 |
| 5,135,517 | 8/1992 | McCoy .................................... 604/281 |
| 5,167,634 | 12/1992 | Corrigan, Jr. et al. ................. 604/160 |
| 5,183,464 | 2/1993 | Dubrul et al. ............................. 128/3 |
| 5,193,533 | 3/1993 | Body et al. ......................... 128/207.14 |
| 5,256,146 | 10/1993 | Ensminger et al. .................... 604/104 |
| 5,263,963 | 11/1993 | Garrison et al. ....................... 606/198 |
| 5,265,606 | 11/1993 | Kujawski ................................ 128/632 |
| 5,267,960 | 12/1993 | Hayman et al. ....................... 604/106 |
| 5,275,610 | 1/1994 | Eberbach ............................... 606/198 |

FOREIGN PATENT DOCUMENTS 9317731  9/1993  WIPO .

*Primary Examiner*—Corrine M. McDermott
*Attorney, Agent, or Firm*—Montgomery W. Smith; Richard D. Allison

[57] ABSTRACT

A method and apparatus for retaining a catheter tip in a fixed position within a blood flow and preventing it from contacting a blood vessel wall. The apparatus includes a tip retainer at the distal end of the catheter that stabilizes the tip of the catheter relative to the blood vessel. The catheter tip is retained within the blood vessel spaced from the wall to ensure that it does not contact the wall of the blood vessel. This reduces damage to the blood vessel caused by chronic movement and contact between the catheter tip and the wall of the blood vessel. In one embodiment, the tip retainer includes a prong that penetrates the wall of the blood vessel, thus preventing the catheter tip from moving longitudinally within the blood vessel. In alternative embodiments, the tip retainer contacts the wall but does not penetrate the wall.

16 Claims, 25 Drawing Sheets

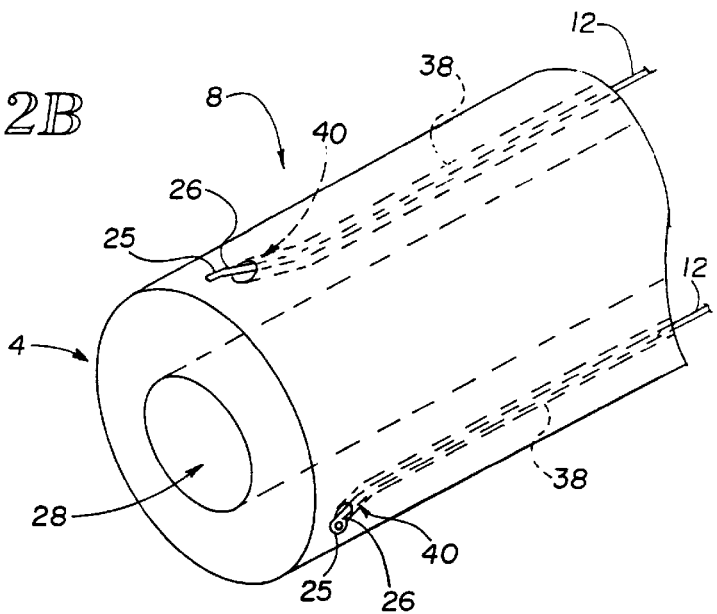
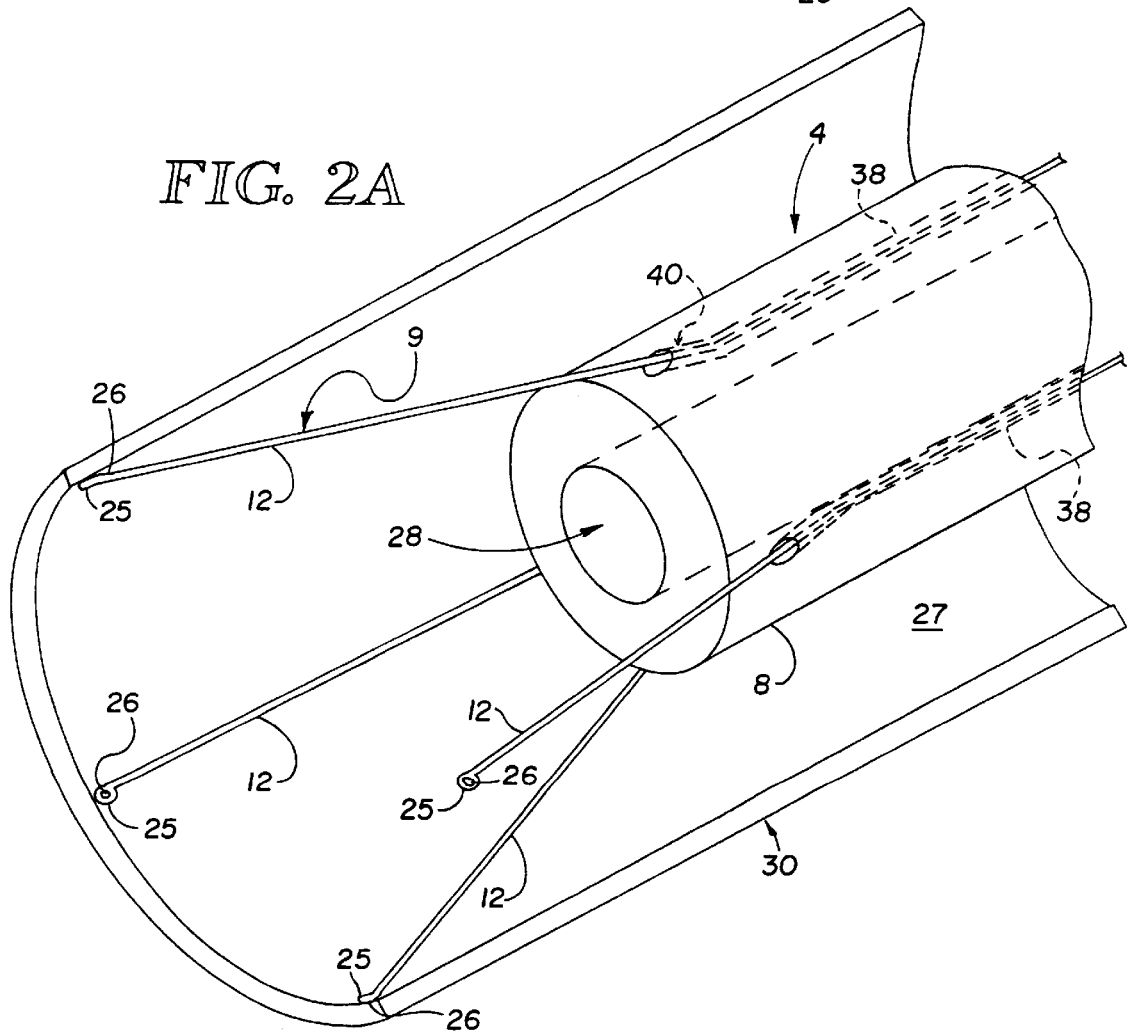

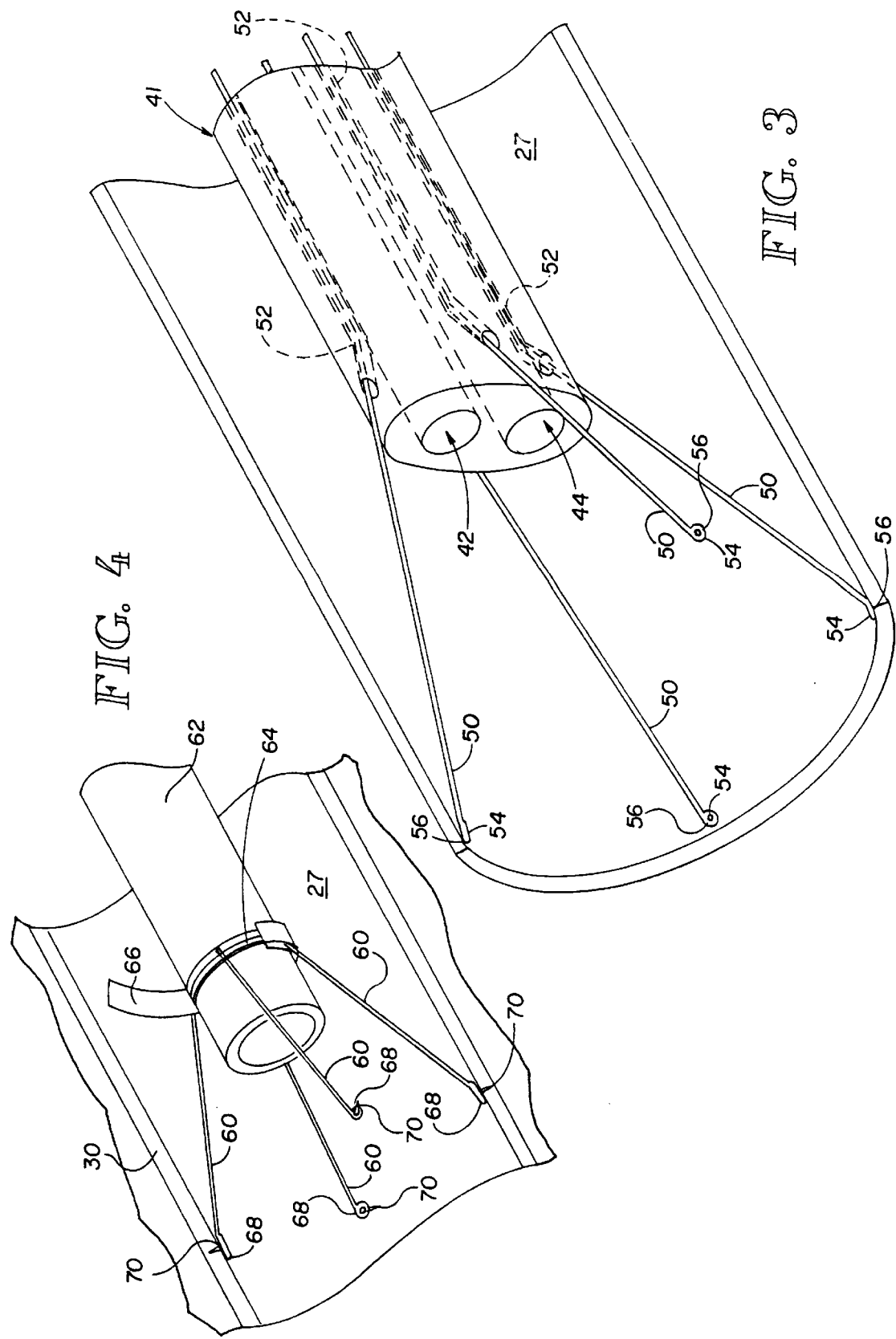

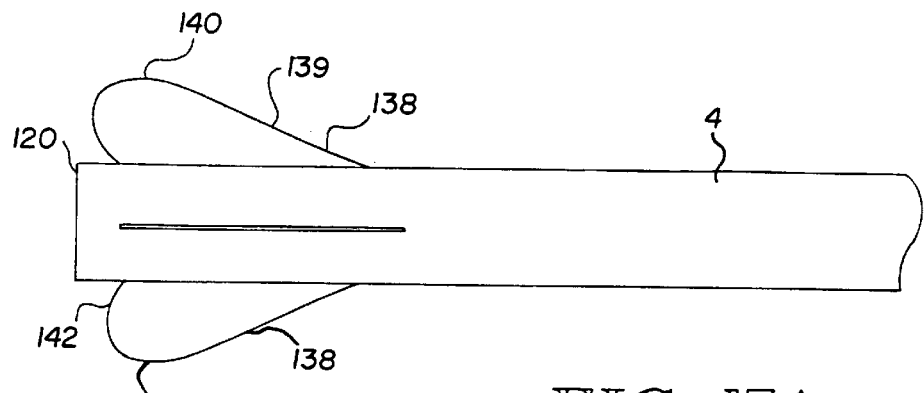
FIG. 17A
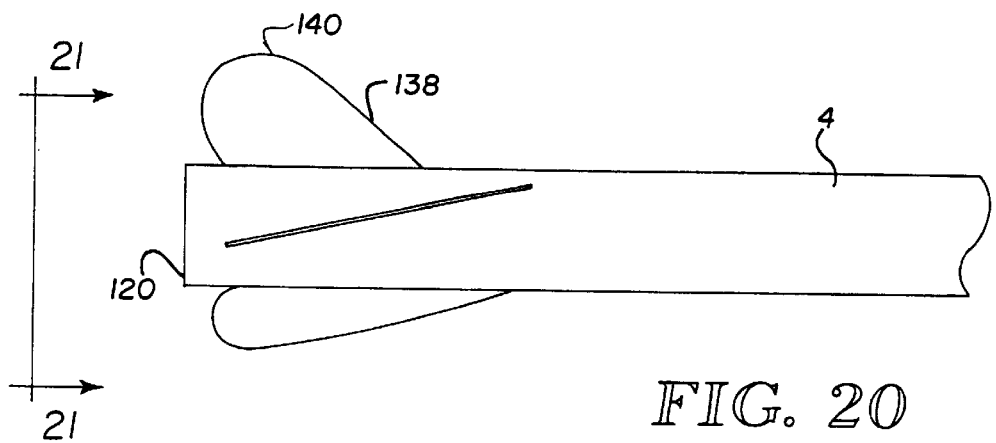
FIG. 20
FIG. 18
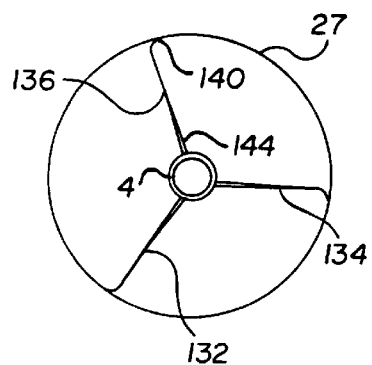
FIG. 19
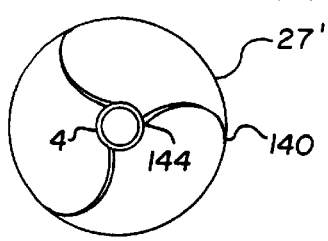
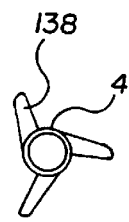
FIG. 21

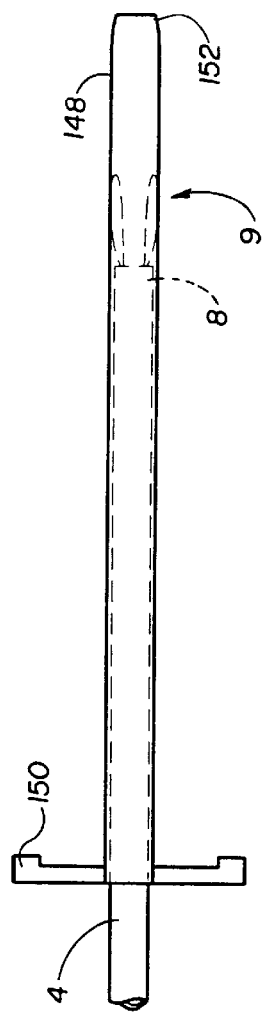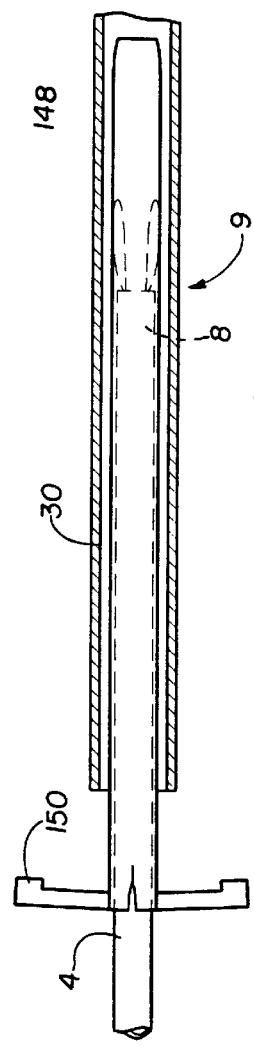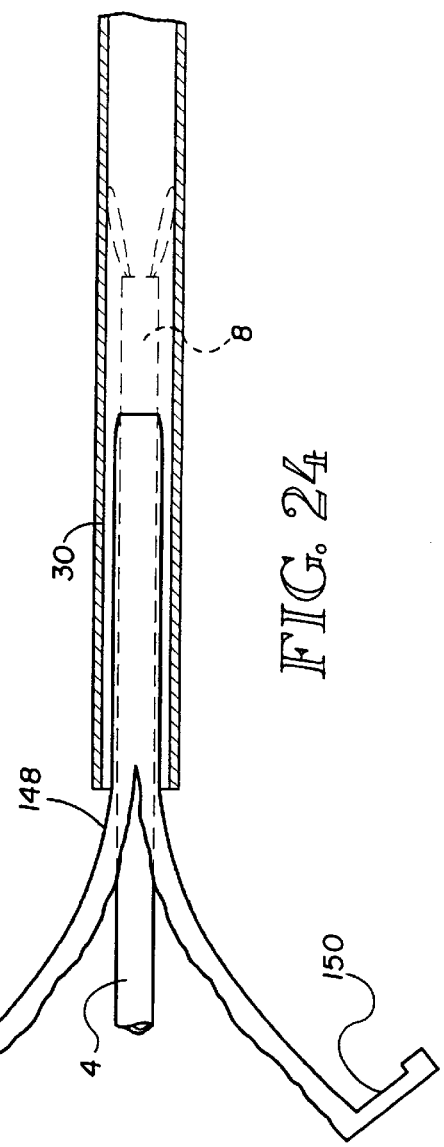

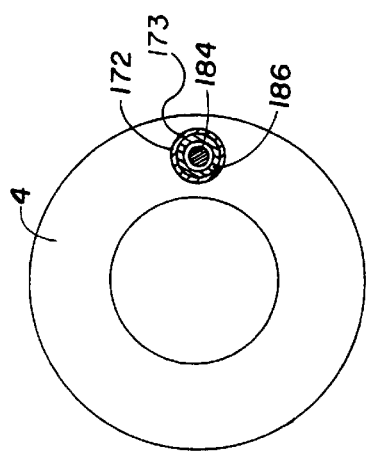
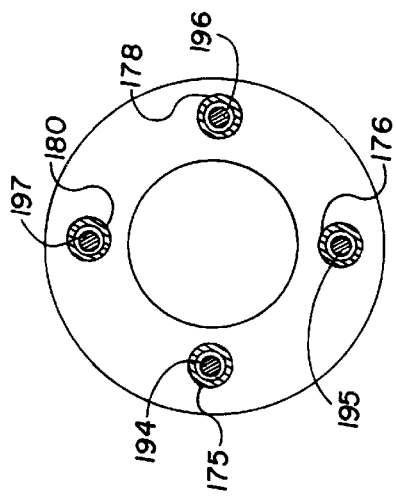
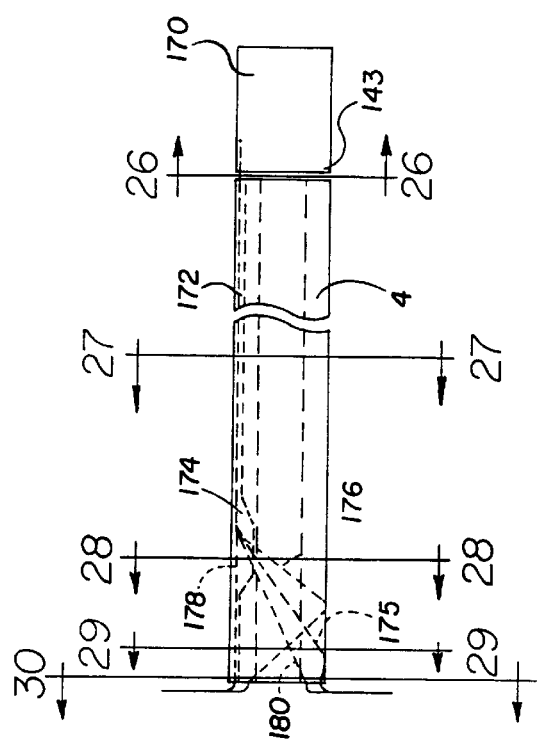
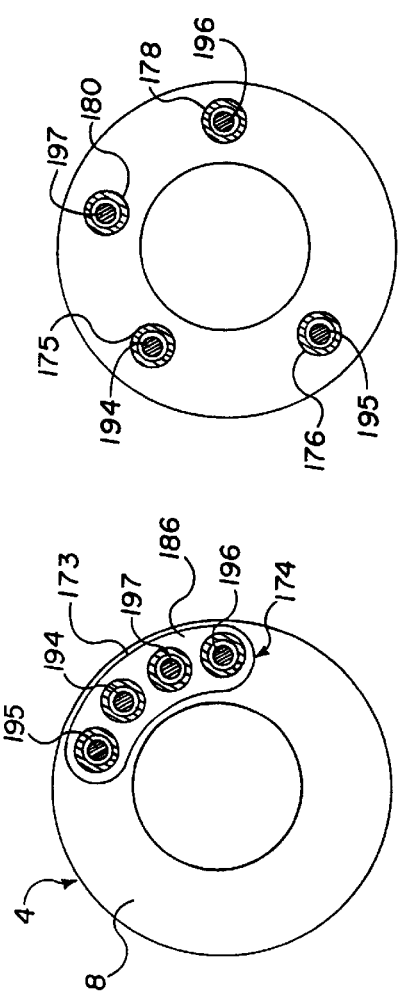

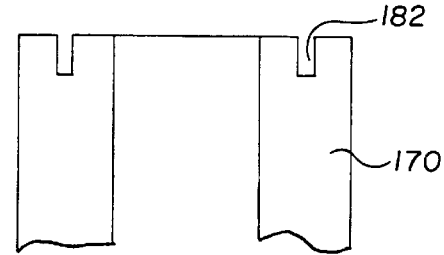
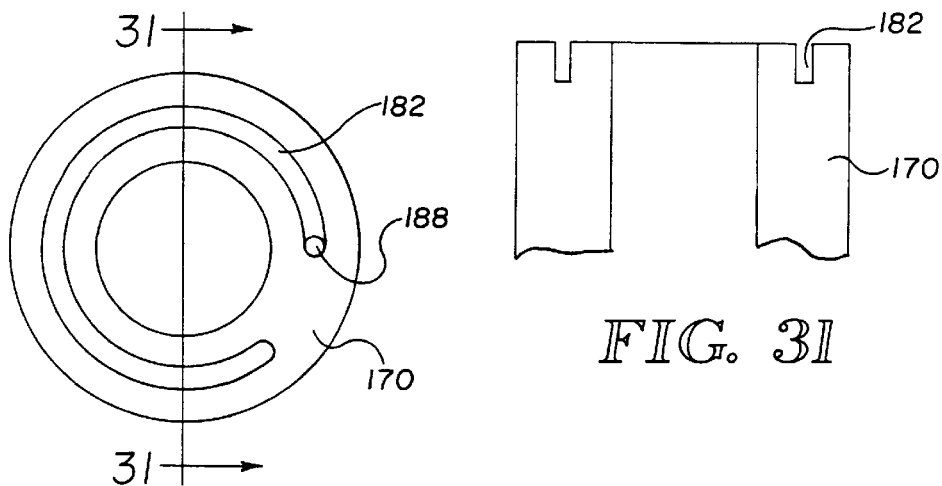
FIG. 31
FIG. 26
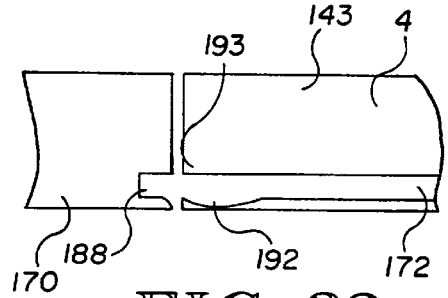
FIG. 32
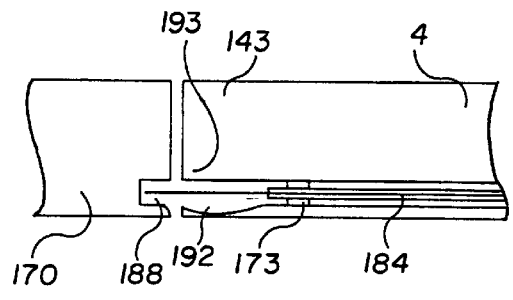
FIG. 33
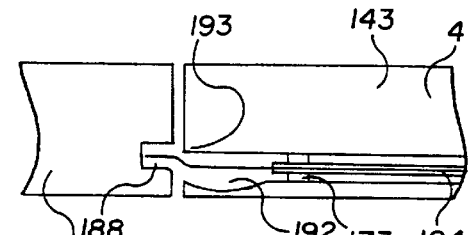
FIG. 34
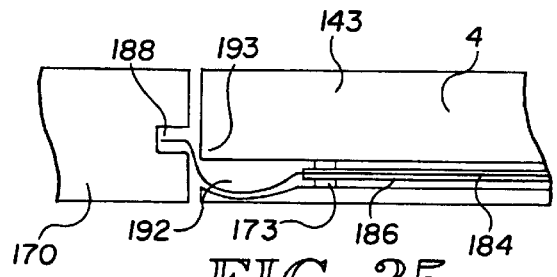
FIG. 35
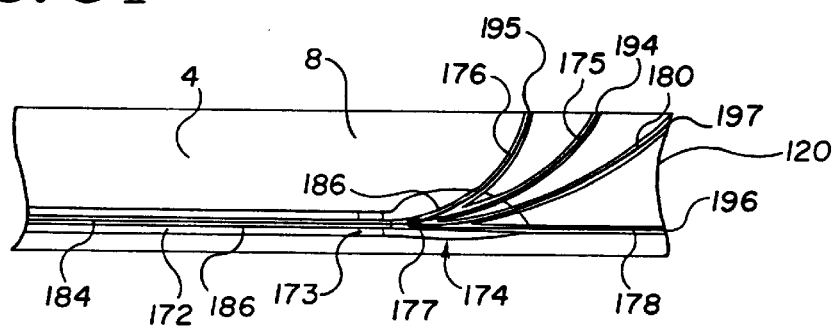
FIG. 36

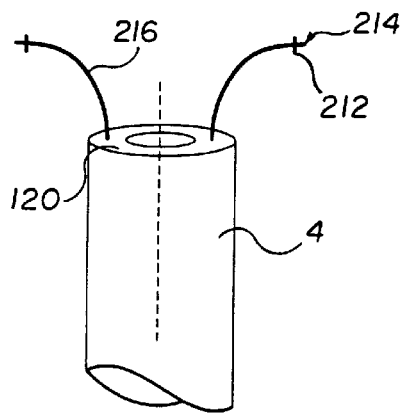
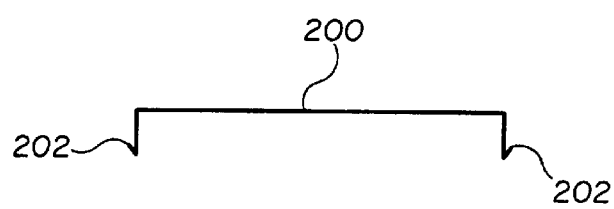
FIG. 46
FIG. 47
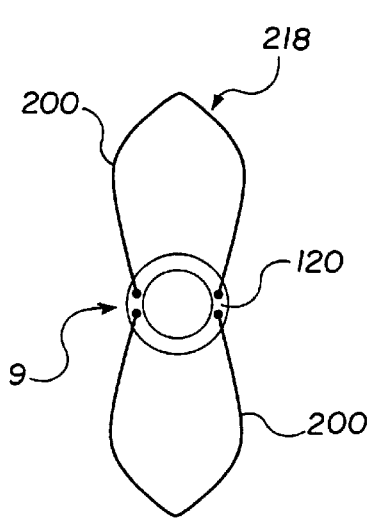
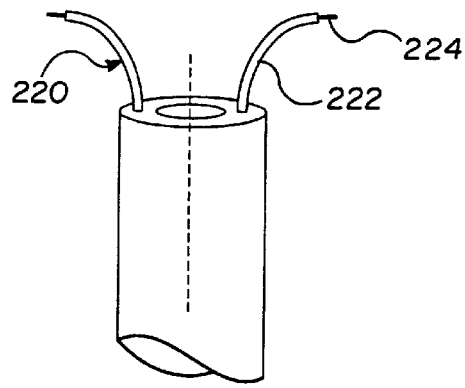
FIG. 48
FIG. 49
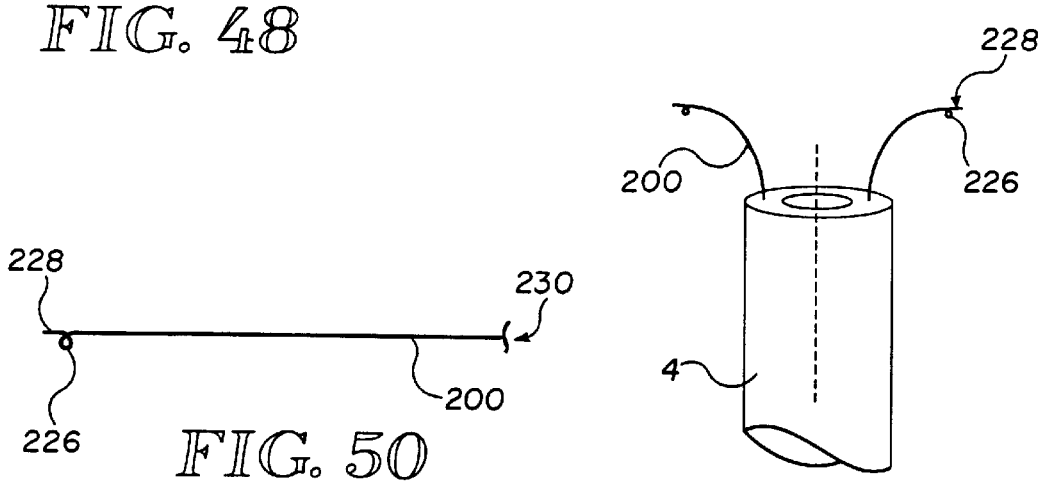
FIG. 50
FIG. 51

CATHETER TIP RETAINER

CROSS-REFERENCE TO RELATED APPLICATION

This application is a continuation of application Ser. No. 08/302,152 filed Sep. 8, 1994, now abandoned which is a continuation of the patent application assigned U.S. Ser. No. 08/137,628 filed Oct. 15, 1993, entitled "Apparatus and Method For Constructing a Tip Retainer For a Catheter, Retaining a Catheter in Blood Vessel in a Fixed Position, and Positioning a Catheter Within a Blood Vessel" now abandoned, which is a continuation in part of Ser. No. 07/844,715, filed Mar. 02, 1992, now abandoned.

TECHNICAL FIELD

This invention relates to the implantation of intravascular catheters that have means for reducing stenosis and thrombosis along the catheter.

BACKGROUND OF THE INVENTION

The treatment of a number of medical conditions requires the placement of catheters within a patient's blood vessel for an extended period of time. These long-term applications include, but are not limited to, blood access for hemodialysis, chemotherapy, parental nutrition, blood transfusions and blood sampling.

Vascular access with catheters was first introduced more than 20 years ago. With the advent of soft, flexible silicone double lumen catheters, both acute and chronic hemodialysis became a routine procedure. Although subclavian dialysis catheters are easily inserted and well tolerated, catheter life span averages about three months. This is of great concern to patients on maintenance dialysis.

It is well known in the medical field that chronic placement of a catheter in a patient's blood vessel often results in catheter failure due to aspiration of the blood vessel wall into the tip of the catheter, clot or thrombus formation at the tip of the catheter, or stenosis around the tip of the catheter. A catheter failure resulting from one or more of these mechanisms is evidenced by an inability to aspirate and/or infuse fluid through the catheter, generally referred to as catheter occlusion. Typically, catheter occlusions caused by aspiration of the blood vessel wall or clot formation at the catheter tip may be resolved by repositioning the catheter tip or infusing antithrombotic agents.

Stenosis is a narrowing of the blood vessel lumen as seen in a venogram and, in general, can be due to either the formation of a thrombus within the blood vessel or a thickening of the blood vessel wall. The generally accepted view is that stenosis around the tip of a catheter implanted within a blood vessel is due to the formation of a thrombus resulting from a biochemical reaction to the introduction of a foreign material into the blood vessel. Previous attempts to prevent catheter occlusion have centered around thrombo-resistant coatings on the catheter surface in order to prevent the biochemical reaction of the patient's blood to the material of which the catheter is formed.

Prior art related to the present invention deals with the placement of stents within a diseased blood vessel to treat the problems associated with stenosis. Stents range from simple wire meshes used in U.S. Pat. No. 4,800,882, to a canister made of hydrophilic plastic which expands upon placement in a blood vessel as in U.S. Pat. No. 4,434,797. Stents are typically secured to a deployment catheter for insertion into the patient's blood vessel via a percutaneous procedure. Surgical placement of these stents is achieved by feeding the catheter from a distant site, e.g., a percutaneous puncture into the femoral artery, to the stenosis target. The deployment catheter is then removed, leaving the stent within the blood vessel lumen.

Prior publications on the subject of mounting devices in the blood stream include "Registration of Phoric Changes of Blood Flow by Means of a Catheter-Type Flowmeter," by Heinz Pieper printed in *The Review of Scientific Instrument* 29(11): 965–967, November 1958, and U.S. Pat. Nos. 4,425,908; 4,936,823; 4,813,930; 5,135,517; and 4,654,028. However, none of these address and solve the problems presented in the field of the present invention.

SUMMARY OF THE INVENTION

The present invention is directed to an intravascular catheter that has means to retain the tip of the catheter within a blood vessel lumen such that the tip of the catheter is prevented from contacting the wall of the blood vessel. This prevents repeated impact between the catheter tip and blood vessel wall. This reduces denudation and damage to the endothelial and smooth muscle cells that line the blood vessel wall. By reducing damage to these cells, the invention allows for the cells to continue to release the bioactive molecules that normally prevent and reverse the thrombotic and coagulation processes in blood.

Most vascular injury research is in the area of arterial injury; however, the mechanism that regulates cellular growth in injured veins is not known. It is a reasonable assumption that the "response to injury hypotheses" proposed in Ross, R., Glomset, J. A., "The Pathogenesis of Atherosclerosis," *N. Engl. J. Med.* 295:369–77, 1976, can also be applied to injuries in the venous system. This hypothesis is based on the following observations after injury to the lumen of the blood vessel: (1) platelet adherence and degranulation precedes smooth muscle cell proliferation; (2) intimal thickening in injured arteries of thrombocytopenic animals is reduced; (3) platelet granules contain potent mitogens for cultured smooth muscle cells. Based upon these observations, Ross and Glomset suggested that a high local concentration of growth factors, particularly platelet-derived growth factors released from degranulating platelets could stimulate smooth muscle cell proliferation. Their hypothesis is based on a relationship between the thrombosis that occurs within an injured vessel and the subsequent cell growth associated with repair of the injured vessel wall.

Normally, hemostasis results from a delicate balance between clot-stimulating and clot-inhibiting processes. Endothelial cells and smooth muscle cells in a normal blood vessel are probably the main source of clot regulating factors such as heparin or heparin sulfate. These heparin and heparin-like molecules prevent the adherence of blood proteins and platelets to the surface of a normal blood vessel. Since the endothelium is a critical component of hemostasis control, localized injury and denudation of the endothelium by repeated impact with a catheter tip results in a shift of this delicate balance toward clot and thrombus formation within a denuded region. This clot formation may occur even if the catheter is composed of a material that normally would not create a reaction in the body.

Physical damage to the wall of the blood vessel affects the release and production of a number of growthstimulating factors such as basic fibroblast growth factor and platelet-derived growth factor. These growth factors help to overcome the antiproliferative activities of the heparin sulfates, thus helping to initiate cellular proliferation and the migration of smooth muscle cells that ultimately leads to stenosis. Therefore, preventing physical damage to the endothelial cell lining of the blood vessel wall reduced stenosis, as well as thrombosis, at the tip of the catheter.

Prior art catheters allow chronic and repeated contact between the catheter tip and the wall of the blood vessel, resulting in damage to the blood vessel as discussed previously. The tip of the catheter may repeatedly bump into different locations inside the blood vessel, or the same location a number of different times, causing a reaction, or worse, damage to the vessel wall. Further damage is caused by the aspiration of the blood vessel wall into the catheter lumen. Additional damage may also be caused by fluid dynamic forces around the openings of the catheter which may occur when blood is withdrawn through or expelled from the catheter, such as in the performance of dialysis.

The present invention solves the aboveidentified problems by approaching them from an entirely different view than the prior art attempts; namely, by preventing repeated impact between the catheter tip and the blood vessel wall. The inventors have found that repeated impact with the vessel wall and a catheter tip, even if it is a soft tip, causes a physical reaction in the blood vessel wall. This reaction occurs because of repeated contact between the catheter tip and the wall of the blood vessel even if the catheter tip is soft, and even if the tip is properly coated with antithrombotic agents. This catheter-induced reaction in the blood vessel wall may lead to the formation of a mural thrombus and/or abnormal cellular proliferation within the blood vessel wall, thus resulting in stenosis and catheter occlusion. Prior art efforts to prevent catheter occlusion through the use of thromboresistant coatings do not alleviate the physical reaction that the catheter tip may cause to the blood vessel wall by repeated impact. Therefore, chronic placement of a catheter in a patient still results in catheter occlusion in the majority of cases.

In accordance with aspects of the present invention, chronic contact between and aspiration of the blood vessel wall by the catheter tip is reduced or prevented altogether. This reduces damage to the endothelial cells lining the blood vessel, thus reducing catheter occlusion due to stenosis and thrombosis. In addition, the occurrence of catheter occlusion resulting from aspiration of the vessel wall or infusions will be reduced.

The present invention includes, in one embodiment, an antistenotic intravascular catheter for insertion into a blood vessel. The catheter includes a tip retainer, located at the distal end of the catheter, for retaining the tip of the catheter within the blood vessel and preventing the catheter from repeatedly contacting the wall of the blood vessel. The tip retainer positions the tip of the catheter within the blood vessel without substantially obstructing fluid flow through the blood vessel. The catheter also includes an internal passageway for permitting fluids to pass through the catheter.

Numerous alternative embodiments are disclosed for the tip retainer. In some embodiments, the tip retainer does not penetrate the wall of the blood vessel. In one embodiment, the tip retainer includes a penetrating member that does penetrate the blood vessel wall.

In all embodiments, the tip of the catheter is retained in the blood vessel by anchoring the tip with respect to the wall of the blood vessel. Advantageously, the tip retainer permits some movement of the catheter tip with respect to the vessel wall, such as slight movement forward and back or side to side with the pulsation of the blood flow. However, movement is restricted to minimize repeated contact (or all contact) of the tip with the blood vessel wall. Just as the anchor of a ship anchors a ship to the bottom but permits some movement of the ship as the water rises and falls or flows, similarly the tip retainer can be said to anchor the tip to the vessel wall but still permit some movement of the tip based on changes of the flow in which it is anchored.

In one preferred embodiment, the tip retainer is two or more loops of wire that flex outward and contact the wall. The loops do not penetrate the wall tissue, but do maintain the tip in a fixed position in the blood vessel, retaining it in the blood flow and preventing repeated contact of the tip with the vessel walls.

In a further embodiment the tip retainer includes fletchings to anchor the catheter tip in the blood vessel. Alternatively, the tip retainer is a plurality of single straight wires that are prestressed to flex outward or straight wires with loops on the end.

In accordance with one embodiment of the invention, the tip retainer includes penetration means for penetrating the wall of the blood vessel and preventing the tip of the catheter from moving longitudinally within the blood vessel. In this embodiment, the tip includes a loop, bead, or other member for limiting the depth of penetration.

In one embodiment of the invention, a plurality of members run from the proximal end of the catheter to the distal end where they extend radially outward until they contact the wall of the blood vessel. In this embodiment, the catheter includes withdrawal means for withdrawing the positioning means into the catheter such that the positioning means is prevented from damaging the wall of the blood vessel when the catheter is withdrawn from the blood vessel. The withdrawal means includes guideways that run from the proximal end of the catheter to the distal end of the catheter. The positioning means extends from the proximal end to the distal end of the catheter within the guideway.

According to one aspect of the present invention, a method for reducing catheter failure due to stenosis or thrombosis at a catheter tip is provided. Positioning means is attached to the catheter tip, and the catheter tip and attached positioning means are placed within the blood vessel without substantially obstructing fluid flow through the blood vessel and such that the catheter tip is prevented from contacting the blood vessel wall.

According to one aspect of the invention, a single, preferably biased, wire extends from the proximal end to the distal end to permit a physician to control the size and location of the loops. At the distal end, the single wire is split into additional wires, or alternatively has a plurality of wires welded thereto to form the tip retaining assembly according to the present invention. Having a single wire extend the length of the catheter provides the advantage that bends in the catheter do not affect one portion of the tip retainer assembly different than other portions of the tip retainer assembly.

According to further aspects of the invention, loops which form the tip retainer assembly are soldered together at the base to provide a more stable and firm loop configuration to solidly retain the catheter within the blood vessel without contacting the wall.

BRIEF DESCRIPTION OF THE DRAWINGS

FIG. 2A is an enlarged perspective view of a first preferred embodiment of the tip retainer as deployed.

FIG. 2B is an enlarged perspective view of the preferred embodiment of FIG. 2A showing the tip retainer after it has been partially withdrawn into the guide tube.

FIG. 3 is an enlarged perspective view of the distal end of a second embodiment of the tip retainer.

FIG. 4 is an enlarged perspective view of an alternative embodiment for connecting the tip retainer to the catheter.

FIG. 17A is a top view of the embodiment of FIG. 15 using fletching attached straight as the tip retainer.

FIG. 18 is an end view of the embodiment of FIG. 17A as installed within a large blood vessel.

FIG. 19 is an end view of the embodiment of FIG. 17A as installed in a small blood vessel.

FIG. 20 is a top view of an alternative embodiment using fletching attached at a cant as the tip retainer.

FIG. 21 is an end view of the embodiment of FIG. 20.

FIGS. 22–24 illustrate a further alternative embodiment for placing the catheter having the tip retainer on the end thereof within a blood vessel.

FIG. 25 is a side view of an alternative embodiment for controlling the tip retainer assembly.

FIGS. 26–30 are cross-sectional views of the embodiment shown in FIG. 25 taken at the positions indicated in FIG. 25.

FIG. 31 is a cross-sectional view taken of FIG. 26 at the point indicated.

FIGS. 32–36 are enlarged views of the extension and retraction control assembly of the embodiment of FIG. 25 to more clearly illustrate its operation.

FIGS. 37–71 illustrate alternative embodiments for the tip retainer assembly 9.

DETAILED DESCRIPTION OF THE INVENTION

Figure 1:
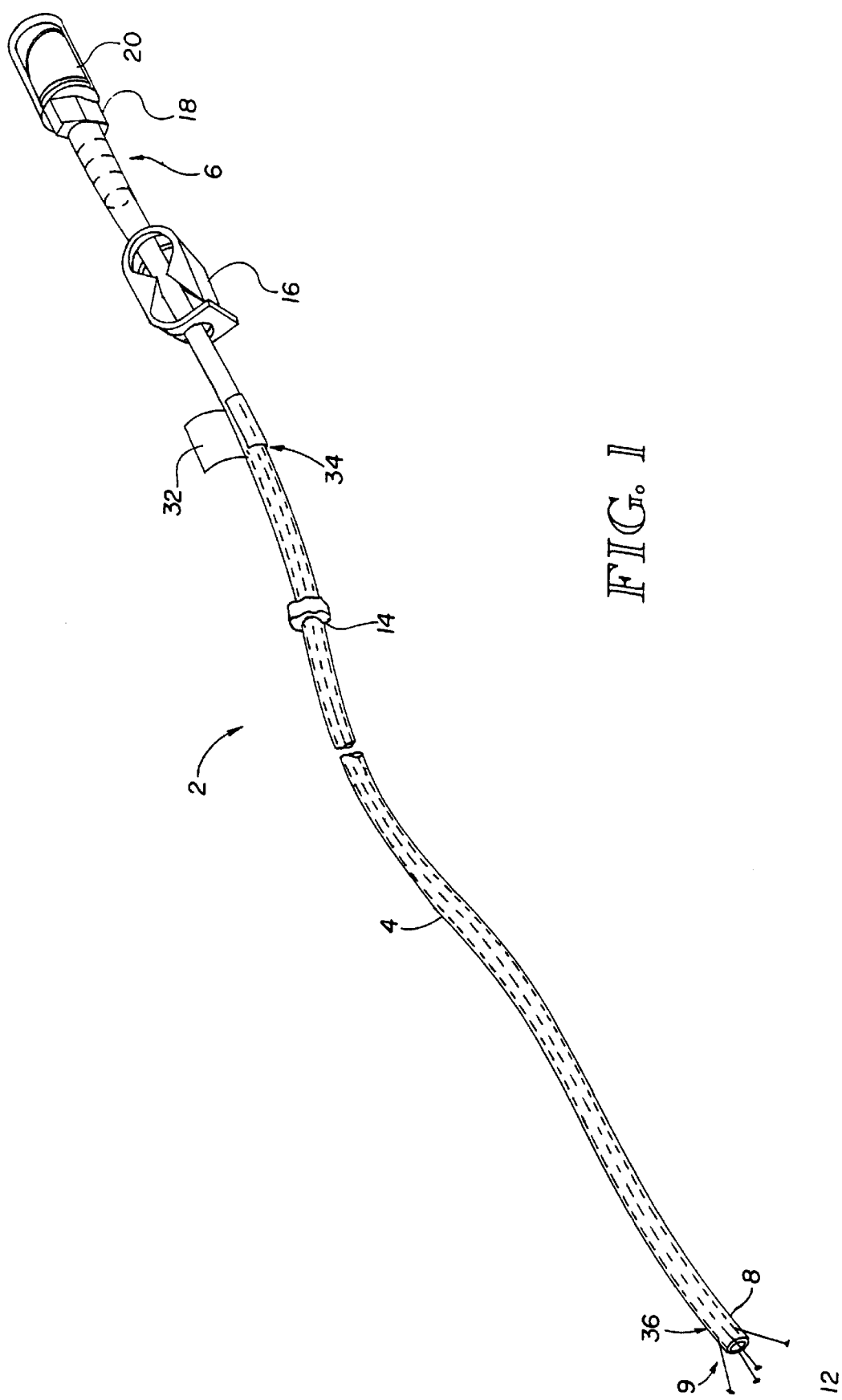
FIG. 1 is a perspective view of a first preferred embodiment of the antistenotic intravascular catheter of this invention.

FIG. 1 is a perspective view of a first preferred embodiment of an antistenotic intravascular catheter 2 of the present invention. Catheter 2 includes a tube 4 formed from a material suitable for placement in a blood vessel, such as silicone rubber. The catheter includes a Dacron anchor cuff 14 for anchoring the catheter subcutaneously. An in-line clamp 16, for preventing fluid flow, is placed on tube 4 adjacent the proximal end 6. The proximal end 6 of the catheter is attached to a luer-lock adapter 18 which is sealed by threading an injection sealing cap 20 onto the adapter in a manner known in the art.

According to one aspect of one embodiment of the present invention, the intravascular catheter 2 includes a tip retainer 9 for retaining the distal end 8 in the bloodstream and preventing the tip of the catheter from contacting the wall of a blood vessel 30 as shown in FIG. 2A.

In a first embodiment, the tip retainer 9 includes four wires 12 positioned within the catheter wall and extending along the length of the catheter, from the distal end of the catheter towards the proximal end 6 of the catheter. This ensures that the proximal ends 34 of the wires 12 will be accessible outside the patient's body after the catheter has been implanted in a blood vessel 30. The proximal ends 34 of the wires 12 are secured to the catheter by an appropriate method such as heat shrink Teflon™ tubing 32 that is placed over the wires and shrunk in place. The proximal end of the wires could also be secured through the use of a band integrally formed in the tube 4 or other structures which prevent movement of the proximal end 34 of the wires 12 until they are controlled by a physician.

The wires 12 are preferably made of or coated with a material which does not cause an adverse reaction when placed in the patient's body. Suitable materials include stainless steel, titanium, some plastics such as nylon, some composite materials, and Teflon™-coated wires, including Teflon™-coated stainless steel. Depending upon the application, the wires 12 have a diameter ranging from 0.0025 to 0.076 cm. In some applications, it may be desirable to treat the wires 12 with an antithrombotic coating, for example, dipping or plating the wires in a coating or applying a coating through plasma polymerization in order to reduce blood clotting on the wires. Plasma polymerization is explained in detail in Yeh et al., "Blood compatibility of surfaces modified by plasma polymerization," *Journal of Biomedical Materials Research* 22:795–818, 1988.

As shown in FIG. 2A, in one embodiment, the wires 12 extend along the length of the catheter through guideways 38 and exit the guideways at openings 40. The guideways 38 protect the wires 12 while also maintaining proper positioning between the individual wires. Guideways 38 and wires 12 are preferably extruded as an integral part of tube 4, or alternatively are extruded individually and are later attached onto the outside of the tube 4 or inserted into tube 4. In the embodiment shown, four wires 12 are used, however, a different number of wires, such as three or five, could be used, depending upon the application.

Preferably, the four wires 12 are equally spaced circumferentially around the distal end 8 such that they serve as a tip retainer 9 and positioning means for positioning the tip of the catheter within the blood vessel 30. The tip retainer ensures that the tip of the catheter does not contact the inner wall 27 of the blood vessel 30. The thin wires 12 restrict movement of the tip of the catheter to prevent it from hitting the inner wall 27 while not substantially obstructing the fluid flow through the blood vessel and not causing clots.

In the embodiment illustrated in FIG. 2A, a loop 25 is formed near the end of each wire 12, and a short penetration prong 26 is formed that extends outwardly from each loop. The prongs 26 penetrate the wall of the blood vessel 30. Each prong 26 is sized and extends from loop 25 such that the prong penetrates the wall of the blood vessel to a depth in the range of 0.1 to 3 mm after placement within the blood vessel. The loops 25 serve as limiting means for limiting the depth to which the prongs 26 penetrate. This prevents the tip 8 of the catheter from moving longitudinally within the blood vessel 30.

Other structures could also be used to perform the penetration and depth limiting functions. As an example, instead of forming a loop near the end of each wire, an enlarged section such as thickening of the wire band welded or bonded to the wire or a bend near the tip of the wire could be used.

The distal end of the catheter is retained within the blood vessel and prevented from contacting the endothelial cells lining the blood vessel by rubbing or aspirating the wall of the blood vessel by the tip retainer 9. Additionally, noncontact damage to the endothelial cells of the blood vessel, such as through fluid dynamics wherein the force of the flow of fluid around the openings of the catheter may cause cellular damage, is believed to be reduced by the present invention. Although penetration of the wall 27 by prongs 26 causes some damage to the blood vessel, the damage caused is not significant in comparison to the damage that would be caused by repeated impact or chronic rubbing of the tip 8 or by aspiration of the inner wall 27, which may occur with prior art catheter designs. By reducing the contact with and damage to the endothelial cells, the present invention allows for the continued release of anticoagulant molecules by the endothelial cells in the vicinity of the distal end of the catheter as explained previously. Correspondingly, there is a reduction in thrombosis and/or stenosis of the blood vessel lumen at the distal end of the catheter and thus reduced catheter occlusion.

The antistenotic intravascular catheter 2 (FIG. 1) may be placed within the blood vessel 30 using a sheath introducer of the type shown in more detail in FIGS. 22–24, an embodiment of which is explained with respect to those figures. In one embodiment, a tubular introducer sheath is inserted within a patient's blood vessel, with the sheath terminating at the point within the blood vessel where the distal end 8 of the catheter is to be placed. The catheter 2 is then placed within the introducer sheath with the wires temporarily constrained along the catheter's longitudinal axis by the sheath. The catheter is then pushed down the sheath until the distal end 8 of the catheter exits the introducer sheath. As the distal end of the catheter exits the introducer sheath, the wires 12 spread radially to contact and penetrate the blood vessel wall as shown in FIG. 2A. After placement of the catheter into the blood vessel, the introducer sheath is removed from the blood vessel.

Another technique for placing the inventive catheter tip retainer within the blood vessel wall is with an inflatable balloon. Small balloons for insertion into the blood stream and methods to inflate them are known in the field of medical treatment devices. According to one aspect of installing this invention, the wires 12 are positioned circumferentially around such a deflated balloon. The balloon is then introduced into the blood vessel by any acceptable technique. When the tip of the catheter is at the proper location, the balloon is inflated and the wires 12 contact the wall 30. In the embodiment in which prongs 26 are present on the ends of wires 12, the prongs are solidly pressed and embedded into the vessel wall 30 under the force of the balloon. The balloon is then deflated and removed. If this installation technique is used, the wires 12 do not need to be spring-biased outward; the force of the balloon will press them outward into contact with the wall 30.

The catheter 2 is removed from the blood vessel by first removing the heat shrink Teflon™ tubing 32 or other structure which secures the proximal ends 34 of the wires. Each wire 12 is then withdrawn from contact with the blood vessel wall 27 into its respective guide tube 38. FIG. 2B shows the wires in this partially withdrawn position. Each wire 12 is withdrawn until the loops 25 and prongs 26 are retracted into the soft silicon rubber that forms tube 4 and guideways 38. After withdrawing each wire 12 into its respective guide tube, the catheter is withdrawn from the blood vessel using standard catheter withdrawal procedures. The ability to withdraw the prongs 26 and loops 25 into the guideways 38 reduces damage to the blood vessel upon removal of the catheter.

FIG. 3 shows the distal end of a second embodiment of the present invention. The second embodiment comprises a tube 41 with an elliptical cross section and two lumens 42 and 44 that run the length of the catheter. The second embodiment is intended to be used for hemodialysis applications in which one of the lumens is used to aspirate blood and the other lumen is used to infuse blood after dialysis. As in the first embodiment, four positioning wires 50 extend the length of the catheter within guideways 52. In the second embodiment, two of the wires 50 are located along the major axis of the elliptical tube 41 while the other wires are located along the minor axis. In this embodiment, the two wires 50 located along the major axis may extend from the tube 41 at a different angle than the two positioning wires which are located along the minor axis. Each wire 50 has a loop 54 and tip 56 near its end. The tips 56 serve as penetration means for penetrating the wall of the blood vessel, while the loops 54 serve as limiting means for limiting the depth to which the tips 56 penetrate.

FIG. 4 shows the distal end of a third embodiment of the present invention. The third embodiment has four positioning wires 60 attached to the distal end 62 through the use of securing hoops 64 and heat shrink Teflon™ tubing 66, which is placed over the hoops and shrunk into place. The combination of the securing hoops 64 and Teflon™ tubing 66 helps ensure that the hoops 64 and wires 60 are securely attached to the distal end 62 of the catheter. In an alternate embodiment, not shown, the wires 60 could be integrally formed into the catheter, thus eliminating the need for securing hoops 64 and tubing 66.

The positioning wires 60 extend radially outward from the securing hoops 64. The wires 60 may be attached to securing hoops 64 by welding, brazing or other appropriate means. In some applications, it may be desirable to treat the wires 60 with an antithrombotic coating to reduce blood clotting on the wires, as explained for the first embodiment. Each wire 60 has a loop 68 formed near the end of the wire, such that a short penetration tip 70 extends outwardly from each loop. The prongs 70 serve as penetration means for penetrating the wall of the blood vessel, while the loops 68 serve as limiting means for limiting the depth of penetration.

This third embodiment of the antistenotic intravascular catheter is inserted into a patient's blood vessel using the same process as described for the first embodiment. Although the third embodiment is structurally simpler than the first embodiment, it requires a more complex procedure in order to remove the catheter from the patient's blood vessel. The third embodiment may be removed using a procedure similar to the catheter insertion procedure described in the first embodiment. A tubular introduction sheath of the type shown in FIGS. 22–24 is placed over the catheter at the location where the catheter enters the blood vessel, and is subsequently slid down the catheter until it reaches the distal end of the catheter. The tubular introduction sheath slides over the positioning wires 60, withdrawing the loops 68 and prongs 70 from contact with the wall of the blood vessel. After withdrawing the loops and tips into the introduction sheath, the catheter is slid within the introduction sheath and withdrawn from the blood vessel. The introduction sheath could be removed during or subsequent to removal of the catheter from the patient's blood vessel.

Figure 5:
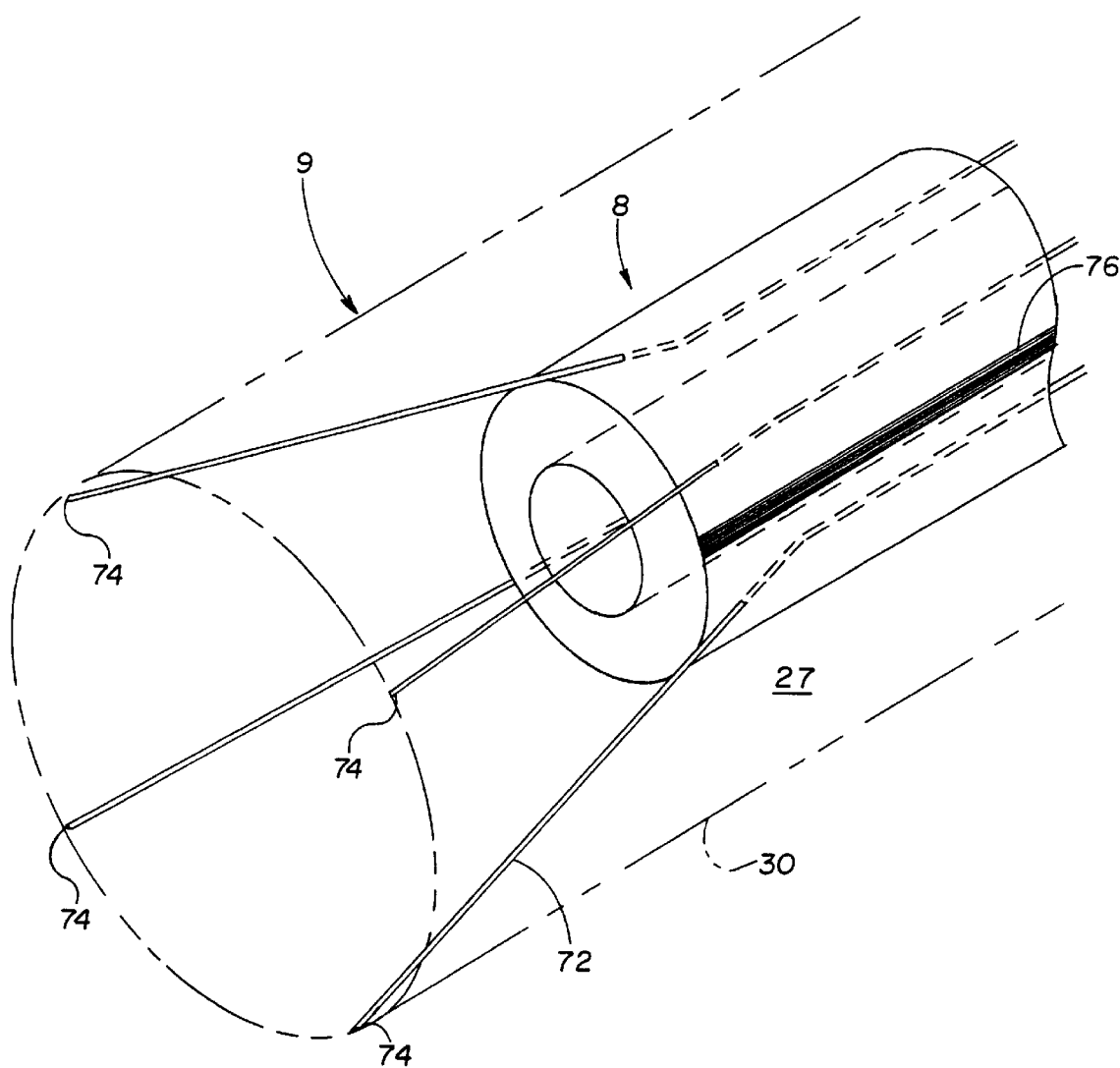
FIG. 5 is an enlarged perspective view of an alternative embodiment of the tip retainer.

FIG. 5 illustrates a tip retainer 9 at the distal end 8 of the catheter constructed according to an alternative embodiment for retaining the catheter tip within the blood flow stream and preventing the tip from contacting the inner wall 27 of the blood vessel 30. According to this alternative embodiment of FIG. 5, the tip retainer 9 includes wires 72 having a blunt terminating end 74 for contacting the inner wall 27 of the blood vessel 30. The blunt end 74 does not include a sharp tip of the type previously described with respect to tips 26, 56 and 70. Instead, the blunt end 74 contacts the inner wall 27 but does not penetrate the wall of the blood vessel 30. The four wires 72 act to anchor the tip of the catheter with respect to the blood vessel wall and retain the tip within the flow in the blood vessel while preventing the tip 8 from contacting the blood vessel wall with the advantages as previously described. The wires 72 are prestressed to be resiliently spring biased outward with an equal pressure from each of the wires 72 such that the tip 8 is generally centered within the blood vessel 30.

An indexing mark 76 is also included on the catheter tube 4, extending along the length of the catheter tube 4. The indexing mark 76 visually indicates to a user the rotational orientation of the tip 8 within the blood vessel and thus indicates the rotational orientation of the tip retainer assembly. The position of the indexing mark 76 may indicate, for example, that the rotational orientation of the tip 8 is such that one of the wires 72 is positioned where two of the blood vessels join together and is not contacting any wall of the blood vessel or providing stabilization. The user may then elect to change the rotational orientation of the tip 8 such that each of the wires 72 is firmly in contact with the blood vessel wall. This visualization could also be done, for example, with the catheter positioned within the introducer sheath.

However, one reason for providing at least three and more preferably four wires 72 is because contact with three wires is generally deemed sufficient to stabilize and retain the tip 8 such that it does not contact the wall 27. For example, the catheter 4 having the inventive tip retainer at the distal end 8 may be positioned at or near the brachial cephalic junction and there is a likelihood that one or more of the wires 12 may fall into the junction. One advantage of having multiple wires is that the tip 8 can be stably anchored even if one of the wires is not anchored to the wall because the other wires will hold it in position. Thus, even if one of the wires 72 is not contacting the blood vessel wall because it is positioned in or along the junction, the other wires 72 will be contacting the wall and will retain the tip 8 in a position to prevent it from repeatedly bumping against the inner wall 27 of the blood vessel 30.

Figure 6:
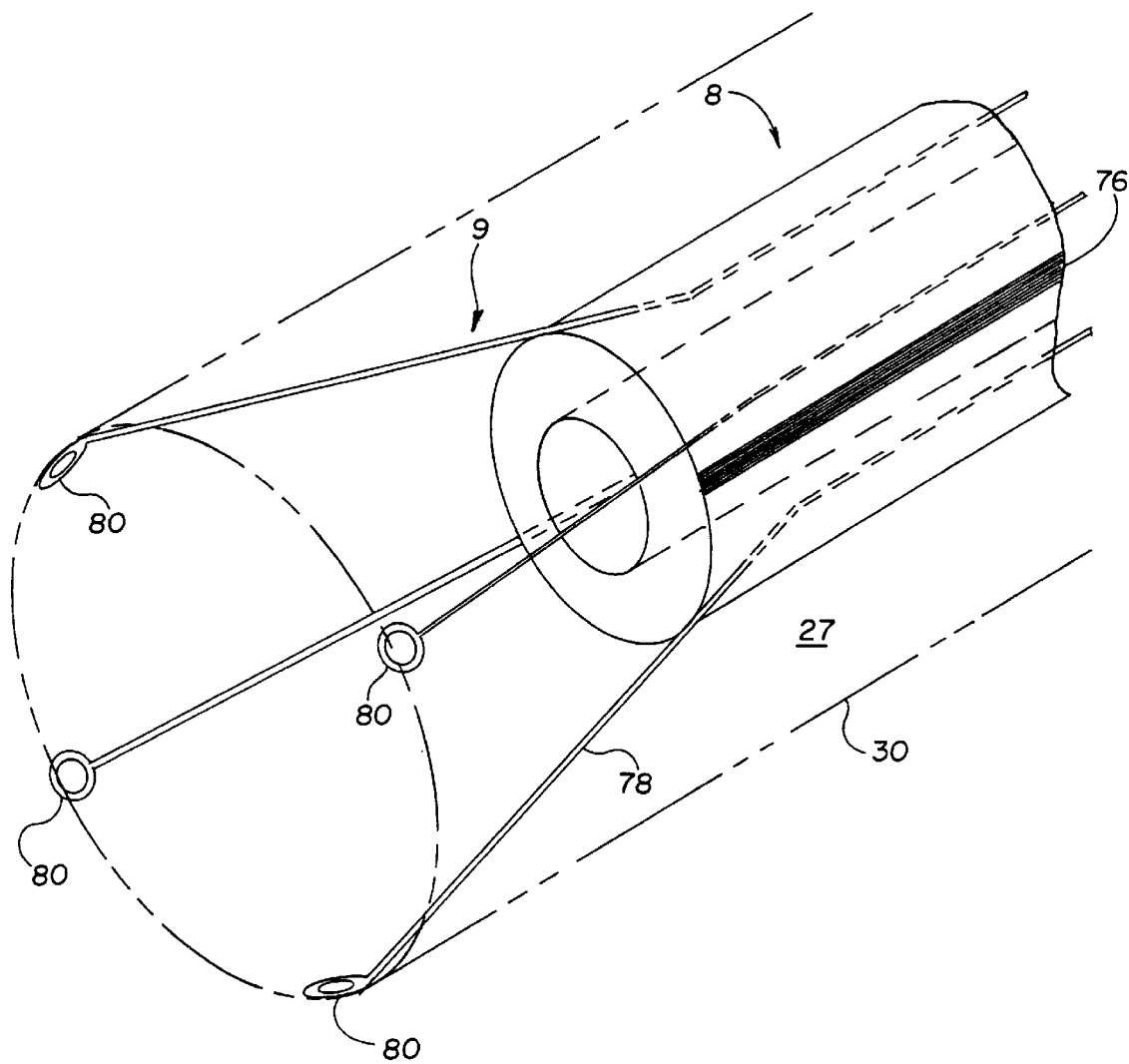
FIG. 6 is an enlarged perspective view of an alternative embodiment of the tip retainer.

FIG. 6 illustrates an alternative embodiment for the tip retainer 9 having wires 78. The wires 78 include enlarged loops 80 at their distal end. The enlarged loops 80 do not penetrate the blood vessel wall 30. Instead, they rest firmly against the inner wall 27, as an anchor to firmly retain the tip 8 in a fixed position within the blood vessel. The loops 80 have an enlarged surface area to ensure that the blood vessel wall 30 is not penetrated while providing a firm support for the tip retainer 9. The loop 80 abuts firmly against the inner wall 27 without penetrating it in a manner similar to the anchor of a ship resting on the sea bottom but not penetrating through the sea floor. The tip retainer 9 in this way anchors the tip 8 without penetrating the wall of the blood vessel 30.

Figure 7:
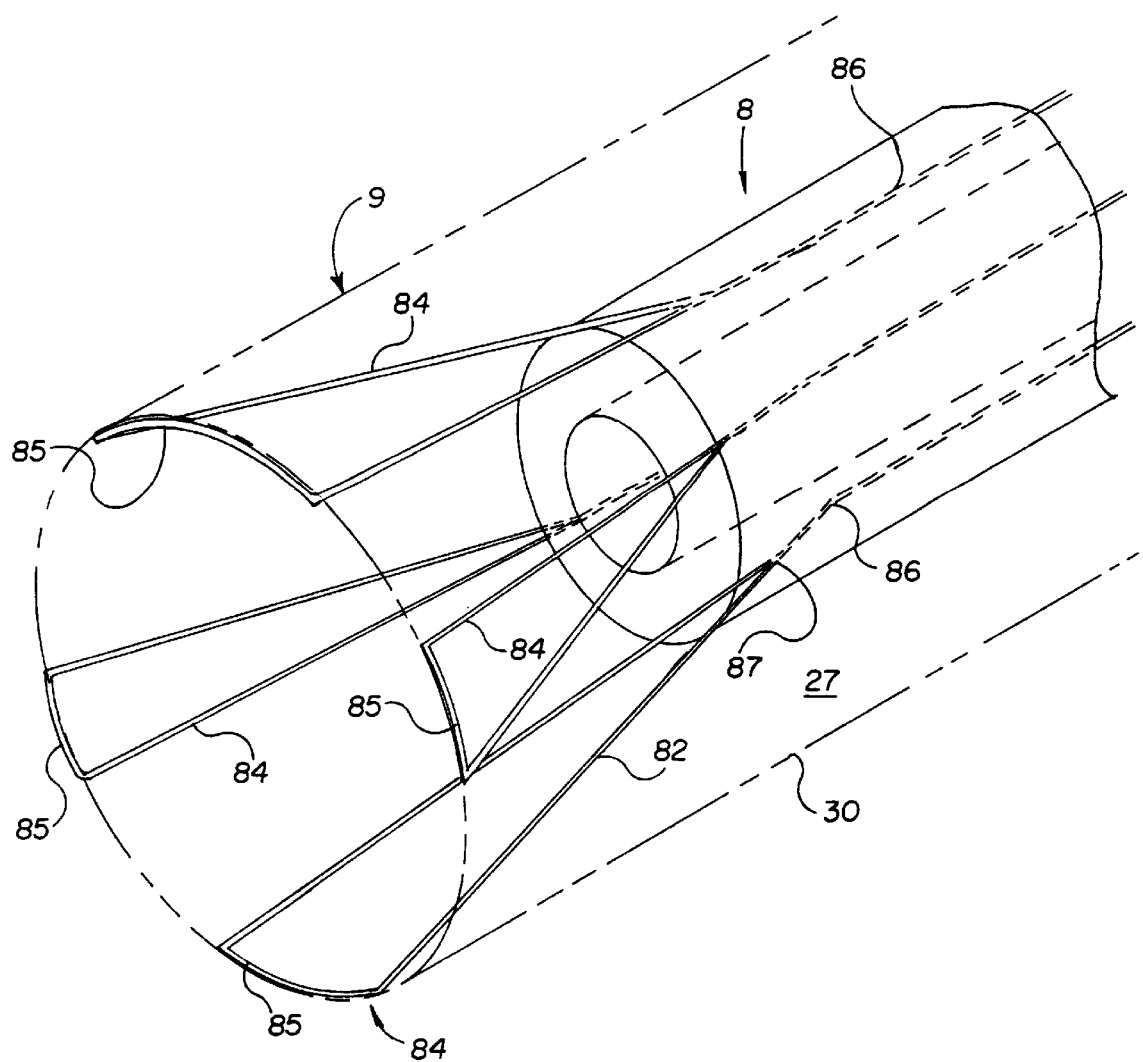
FIG. 7 is an enlarged perspective view of a further alternative embodiment of the tip retainer.

FIG. 7 illustrates an alternative embodiment of the tip retainer 9 having wires 82 formed in an enlarged loop 84. The loops 84 are formed from a single piece of wire that is bent at the end and terminates by being contacted to itself at the end 87, a single wire being within the guideway. Alternatively, the loop 84 is formed from the wire 82 being bent in half and having two sections of the wire 82 extend within the guideway 86. The two ends of the wire 82 extend out of the proximal end of the tube 4 at position 34 as shown with respect to FIG. 1. The wires 82 can therefore be extended or retracted, according to the user's preference, to provide loops 84 of a desired size and shape. The wires of the loops 84 are prestressed or bent to be resiliently spring biased outward so they extend with equal force and equal distance from the tip 8 so as to retain the tip 8 in approximately the center of the blood vessel 30. Use of loops 84 provides the advantage of broad contact area 85 with the inner wall 27 while ensuring there is no penetration of the wall. The broad contact area at a distal region of each of the loops 84 is a further aid for centering the tip 8 and ensuring that it is firmly retained within the blood flow and the blood vessel and does not contact the inner wall 27.

Figure 8:
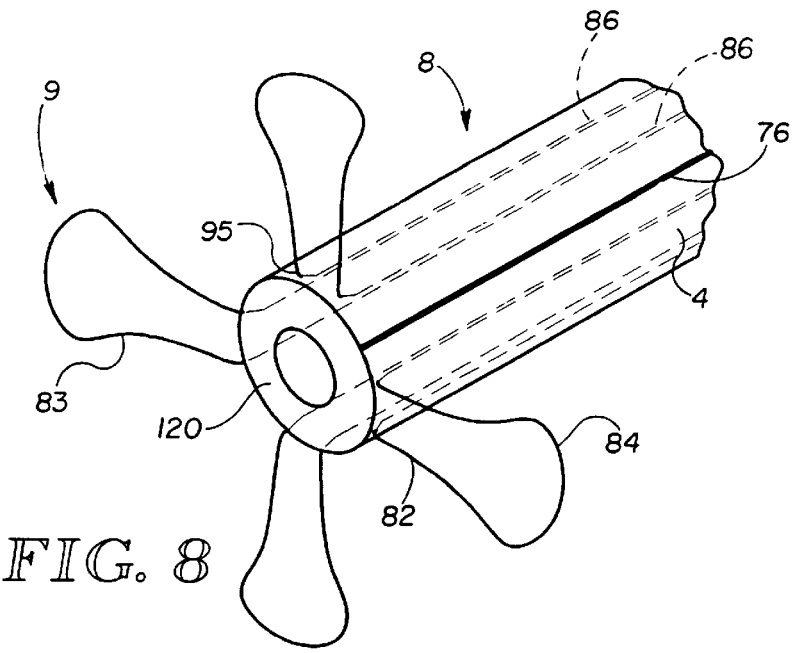
FIG. 8 is an enlarged perspective view of a further alternative embodiment of the tip retainer.

FIG. 8 is an alternative embodiment generally along the lines of FIG. 7 with the loops 84 formed in a cloverleaf arrangement. The cloverleaf shape of the wires 84 serve to further increase the contact area and provides strength in anchoring the tip 8 of the catheter 4 within the blood vessel but without penetrating the wall of the blood vessel. In one embodiment, the loops exit from the tip region 8 a selected distance 95 back from the end of the tip. Having the wires exit spaced apart from the tip end 120 decreases the risk of creating blood clots at the end 120 or forcing the lumen shut at the face 120 under a heavy spring force by the wire loops 84. The end region 8, particularly the face 120, may be constructed of a somewhat stiffer material to keep the lumen opening from being partially closed when the wire loops 84 are deployed.

In the cloverleaf arrangement of FIG. 8, each end of one wire extends down its own guideway 86, or alternatively multiple wires may extend down the same guideway 86, permitting user manipulation of individual wires. The wires may exit from the face 120 of tip 8, or, as shown, exit from a location along the sidewall and extend forward, toward the tip.

Figure 9:
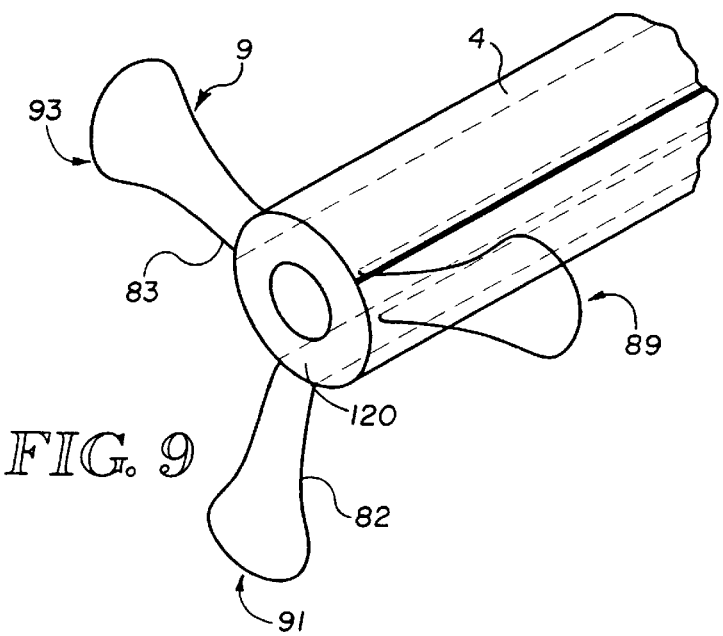
FIG. 9 is an enlarged perspective view of a further alternative embodiment of the tip retainer.

FIG. 9 illustrates an alternative embodiment for the tip retainer 9 of a three-leaf clover configuration. Three loops 89, 91, and 93 are provided that extend out of the surface of tip end 120 if desired. The three loops 89, 91, and 93 are positioned equidistant around the catheter tube 4. Using three wires provide the advantage of fewer wires in the blood flow, but still produces sufficient force for anchoring. For example, as previously discussed with respect to FIG. 5, the catheter may be installed such that the tip is at or near the brachial cephalic junction. Even if one of the loops 89 falls into the junction itself, the other two loops 91 and 93 will contact the wall and provide a stable contact to anchor the tip 8 within the vessel. The term anchor is used in this embodiment and all others herein in the broad sense of providing a general positioning of the catheter in the blood vessel. Some slight movement from side to side or back and forth is permitted by the various tip retainers as they anchor the tip 8 to the wall, just as a ship's anchor permits some ship movement but holds it generally in position.

The wires 82 of loops of FIGS. 8 and 9 are formed with a preselected resilient bias outwards as determined by their shape and construction. In some embodiments, a very light spring action is provided by having a light, resilient bias outward so that the device may be used in a wide range of size of blood vessels, from very small to very large, with assurances that the blood vessel wall will not be penetrated. In the embodiment of FIGS. 8 and 9, the spring bias force outward is easily adjusted by varying the angle of connection between the straight portion within the guideway and the loop portion 84. For example, the angle at which the straight portion 83 extends from the tip 8 can be selected at a desired angle.

One distinct advantage of the present invention over the prior art is that the catheter end 8 is retained within the flow of the blood and prevented from contacting the wall of the blood vessel without holding the catheter end 8 absolutely rigid. According to some prior art techniques, such as that described in the article of Pieper, as discussed in the background of the invention, the concept is to hold the tip as rigid as absolutely possible. While this may have some benefit in some embodiments, one distinct advantage of the present invention is that the invention will still operate properly even if the tip is permitted to move to different locations within the blood vessel. For example, the tip 8 may move to one side or the other within the blood vessel, based on movement of the patient, or of a rubbing of the blood vessel. Additionally, the tip 8 may move longitudinally, along the direction of the blood flow as the blood pulses. This is desirable in many embodiments and may actually act to relieve some of the stress created by the presence of the catheter. The tip retainer 9 includes members having a light spring force which permits some relative movement between the catheter tip 8 and the wall 27 of the blood vessel. However, the springs have sufficient force that the catheter tip rarely actually contacts the blood vessel wall, thus preventing damage to the blood vessel wall. In some of the embodiments described herein, the spring force becomes stronger as the catheter tip approaches the wall, thus serving to maintain the catheter tip in a spaced relationship from the vessel wall, even if some force is acting on the catheter tip 8 to push it toward the wall. The light spring force at an extended location of the spring permits some catheter tip movement, but as the catheter tip becomes closer to the wall, the spring force gradually increases, making it more difficult for the catheter tip to actually contact the wall. In some embodiments disclosed herein, the spring force is sufficiently strong that as the catheter gets extremely close to the wall, it is forced back with significant pressure to prevent an actual impact with the wall.

As will be appreciated, the tip retainer assembly 9 of each of the embodiments described herein may be made of or coated with an appropriate antithrombotic material that does not cause an adverse reaction when placed within a patient's body, as previously described.

The physician extends or withdraws the wires in the embodiments of FIGS. 1–9 to contact the blood vessel wall with the desired force. If the vessel wall has a large diameter, the wires are extended further. Similarly, if a high retaining force is desired, the wires can be extended slightly farther. On one hand, if the physician encounters a small vessel, or one in which a weak retaining force is sufficient to anchor the tip 8, he may withdraw the wires as necessary.

The physician also selects a catheter tip having a properly sized and spring biased tip retainer assembly 9 for his intended uses. If the spring force is found to be too weak, or alternatively, too strong, he may select another tip that is manufactured having a tip assembly 9 of a slightly different spring force, as necessary. (This may be done for each of the embodiments described herein, as desired.) Similarly, a range of loop sizes and shapes is provided to permit the physician to select the one that best suits the needs of a particular use.

The physician may observe the placement and operation of the catheter tip inside the blood vessel to ensure that it is properly anchored as the procedure progresses. This observation can be carried out with known ultrasonic imaging equipment, for example. Alternatively, the tip 8 may have a radioactive isotope or other marker placed therein to permit the physician to ensure that the tip is immobilized and not contacting the vessel wall. A fluoroscope or X-ray device may also be used to image the tip.

Often the tip must be in position in the blood vessel for an extended period. Solid placement of the tip in a position which is spaced from the wall and securely anchored with respect to the wall followed by confirmed observation of this by a physician is thus helpful to permit long-term placement of the catheter without injury to the blood vessel.

Figure 10A:
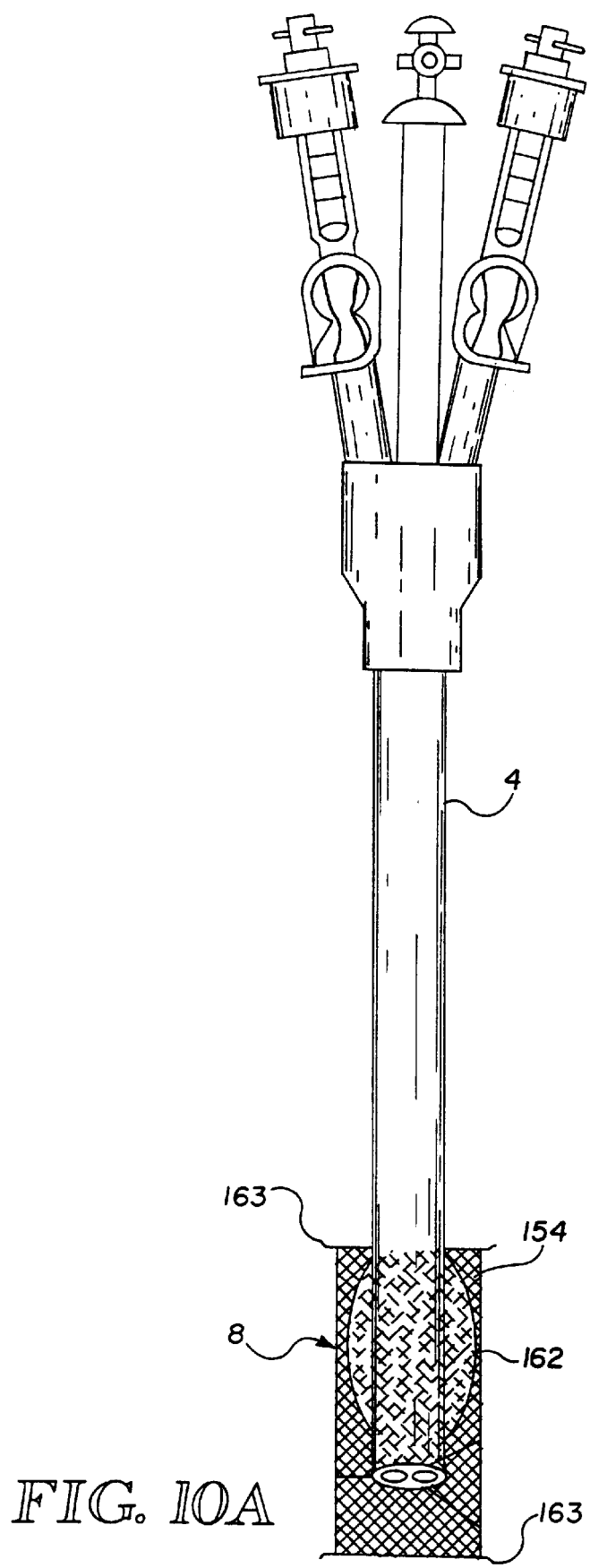
FIG. 10A is an enlarged perspective view of a further alternative embodiment of the tip retainer.
Figure 10B:
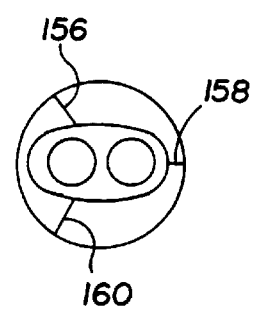
FIG. 10B is an end view of the device of FIG. 10A.

FIGS. 10A and 10B illustrate a further alternative embodiment of the invention. According to this alternative embodiment, an intravascular stent 154 is provided at the distal tip 8 of the catheter 4 for the prevention of stenosis and subsequent catheter occlusion. The stent 154 is an intraluminal vascular prosthesis constructed of braided stainless steel, or other materials. They are, of course, coated with the appropriate materials to prevent interaction with the blood. Current applications of a standard stent include placement in the urinary system, and more recently, within arteries for arterial and coronary disease as an intraarterial wall support usually following balloon angioplasty.

To deploy the stent according to the invention, an expandable balloon 162 is positioned near the tip region 8 along the outer wall of the catheter 4, or alternatively, a rolling membrane is provided around the stent 154 and constructed near the catheter tip. The balloon 162 is covered with the self-anchoring stent 154, the entire assembly being attached along the sidewall of the catheter tube 4 when it is inserted into the blood vessel. After the catheter 4 has been inserted into the blood vessel with a tip 8 at the desired location, the balloon 162 is inflated to deploy the stent 154. The stent 154 includes prongs 163 that penetrate the wall of the blood vessel to solidly affix the stent 154 and the catheter end 8 to the wall of the blood vessel. The balloon 162 is then deflated. The stent 154 is connected to the catheter tip 8 by one or more anchoring wires 156, 158, and 160. If desired, to facilitate catheter removal, the prongs 163 may be connected to the stent 154 with prestressed breakaway points so that they may be easily broken off and the stent 154 removed. The prongs 163 may be composed of a material which is absorbed by the body over time. Alternatively, the wires 156, 158, and 160 which connect the tip 8 to the stent 154 may have prestressed breakaway points at the surface of the stent, interfacing between the catheter and the stent 154. The catheter 4 may be removed by withdrawing it, applying pressure to sever the prestressed breakaway points near the surface of the stent 154. In this embodiment, the stent 154 remains within the body and, is preferably constructed of a material which can be absorbed by the body over time rather than being constructed of stainless steel. Materials which can be absorbed by the body are well known in the art and any of those which is commonly known is acceptable for use to construct stent 154 or prongs 163.

According to the embodiment of FIGS. 10A and 10B, the stent 154 is preferably a braided mesh, or an alternative embodiment, includes a slit extending longitudinally along its entire length. Having a slit in the stent 154, or alternatively constructing it of a braided material permits the stent to be completely collapsed, in a tight position around the catheter 4 and then expanded by balloon 162 to have enlarged diameter along the inside surface of the blood vessel.

By using the techniques according to the concept of this invention, as disclosed in FIGS 10A and 10B, as well as all other figures of this invention, the catheter tip 8 is anchored, preventing damage to the blood vessel wall and thus preventing cellular proliferation and stenosis.

Figure 11:
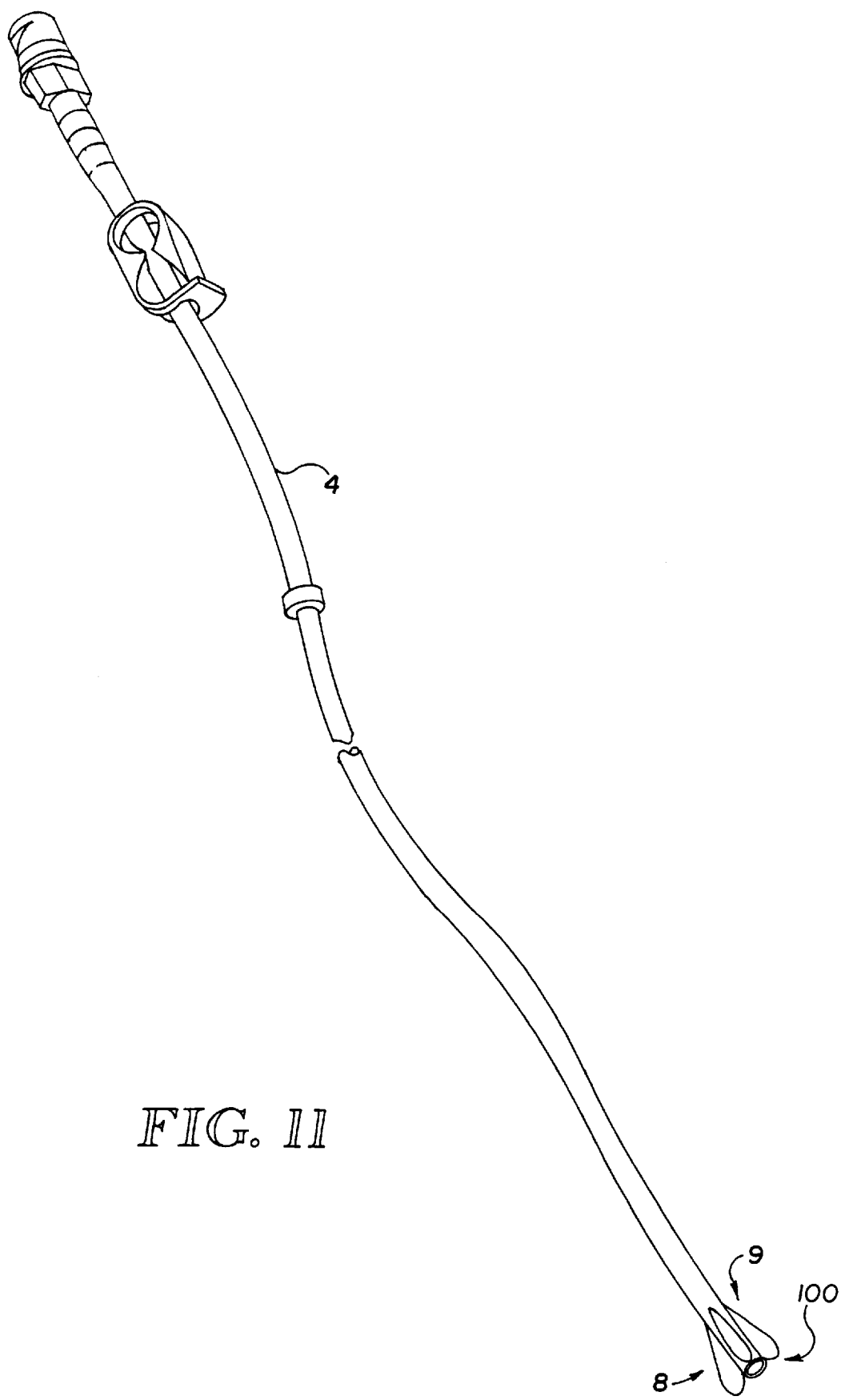
FIG. 11 is a perspective view of a further alternative embodiment of the catheter showing an alternative embodiment of the tip retainer.
Figure 15:
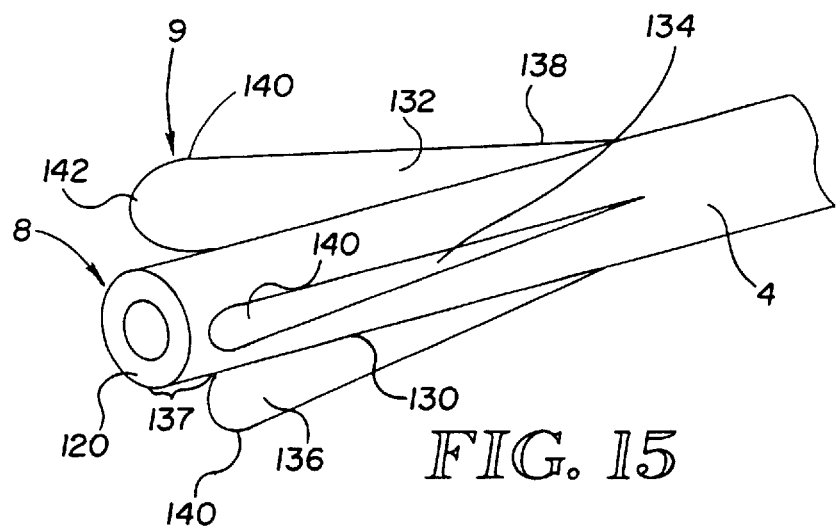
FIG. 15 is an enlarged view of a further alternative embodiment of the tip retainer.
Figure 16:
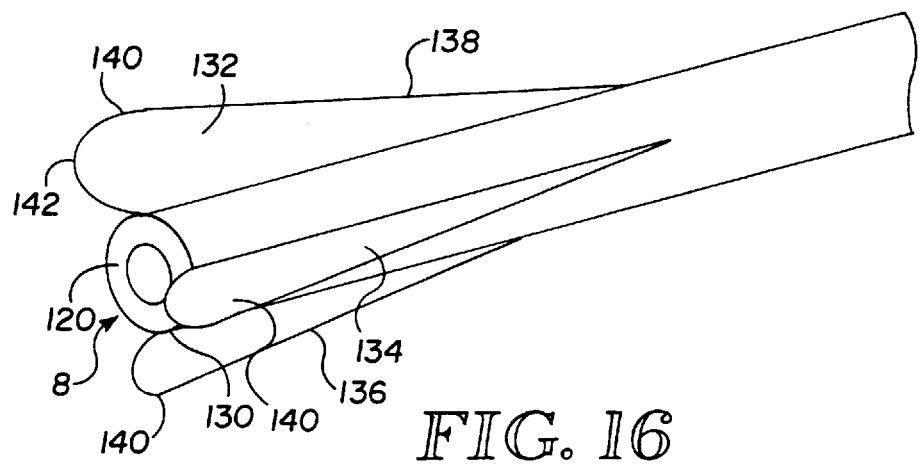
FIG. 16 is an enlarged view of a further alternative embodiment of the tip retainer.

FIG. 11 illustrates a further alternative embodiment of the catheter having a tip retainer 9 at a distal end thereof composed of fletching 100. The fletching 100 is positioned adjacent to the tip 8 or, in one embodiment, recessed back from the tip portion 8 a slight distance as shown in FIGS. 15 and 16 and explained in more detail herein.

An advantage of the use of fletching 100 is that the tip retainer 9 is constructed in which the fletching 100 is a plastic or polymer which is injection molded. In one preferred embodiment, the fletching 100 is injection molded or extruded simultaneously with the injection molding or extruding on the tube 4 so that the manufacturing cost is minimized and the entire assembly is provided as a single, unitary member.

Figure 12:
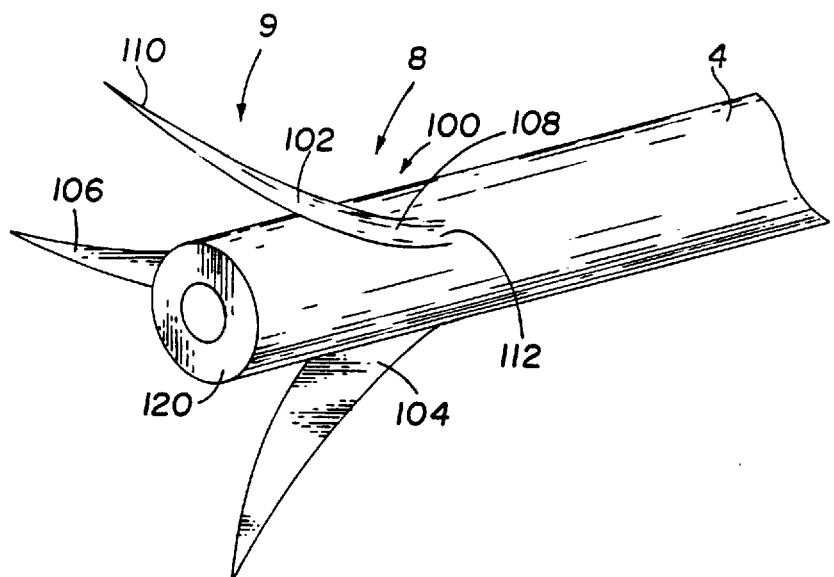
FIG. 12 is an enlarged view of a further alternative embodiment of the tip retainer.
Figure 13:
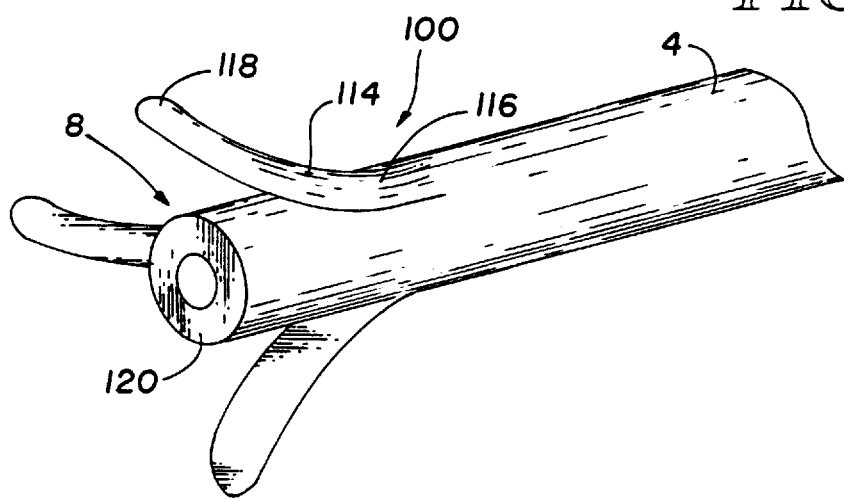
FIG. 13 is an enlarged view of a further alternative embodiment of the tip retainer.
Figure 14:
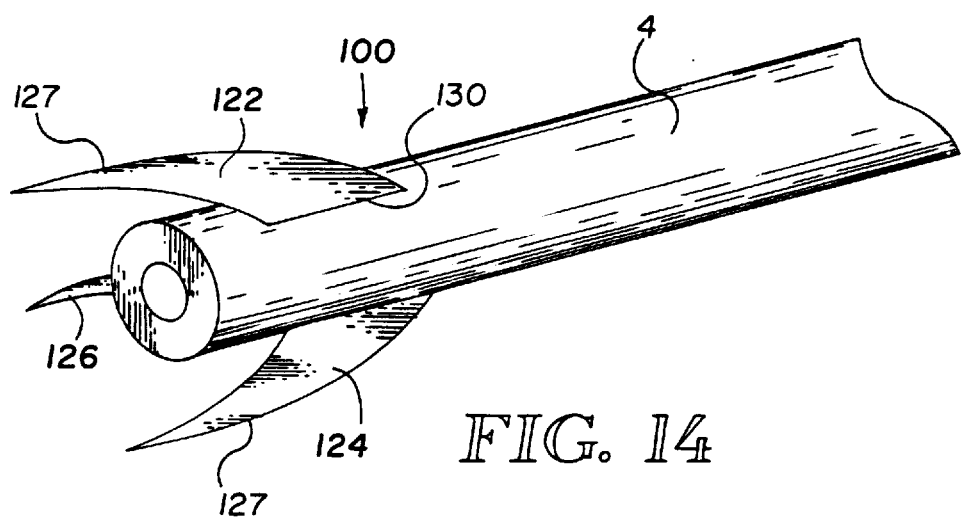
FIG. 14 is an enlarged view of a further alternative embodiment of the tip retainer.

FIGS. 12–14 illustrate alternative embodiments for the shape of the fletching 100 which provides the tip retainer assembly 9. According to the embodiment of FIG. 12, three fletchings are provided, 102, 104 and 106. The fletching 100 is composed of the same material as the tube 4, being constructed from a unitary member in a preferred embodiment. In the embodiment of FIG. 12, the fletching 102 contains a flat surface region 108. The flat surface region 108 extends circumferentially along the same radius of the catheter 4. That is, the flat surface 108 faces upward, presenting a planar surface generally at a tangent to the circular catheter 4. The fletching 102 then extends upward, away from the tip portion 8, narrowing to terminate in a tip region 110. The fletching 102 has a preselected resilient spring bias outward as it extends upward from a base region 112 towards the tip region 110. The tip region 110 contacts the wall of the blood vessel but does not penetrate the wall. The contact at the tip 110 performs the function of anchoring the tip 8 with respect to the blood vessel wall so that the tip 8 is retained in a fixed position with respect to the blood vessel wall, without contacting the wall and remaining within the blood flow. In a preferred embodiment, three fletchings are provided, 102, 104 and 106, each constructed similarly to that which has been described in detail with respect to fletching 102 and each providing a similar spring biased force outward to center the tip portion 8 within the blood vessel.

According to the embodiment as shown in FIG. 12, the tip portion 110 of each of the fletchings 102, 104 and 106 is positioned beyond the end of the tip region 8, so that the anchoring position is beyond the distal end of the tip portion 8. Providing fletchings 102, 104 and 106 that extend beyond the tip 8 is easily provided during the manufacturing process during the molding or extruding of the tubing 4, or alternatively by cutting the tip short after the extruding process so that the tip 110 extends beyond the end of the tip 8.

In an alternative embodiment the fletchings 100 are positioned such that the tip portion 110 of the fletching 102 that contacts the blood vessel wall is approximately at the end of the tip portion 8 as explained with respect to other alternative embodiments herein.

FIG. 13 shows an embodiment in which a fletching 114 has a flat planar portion 116 in generally the same orientation as the planar portion 108 of fletching 102. That is, the fletching extends flat with respect to the tubing 4, generally in the same circumferentially extending radius as the tubing 4. However, the fletching 114 has a rounded tip portion 118 providing a broader contact surface for anchoring the tip region 8 with respect to the blood vessel wall. The broad surface area 118 provides a large contact surface area to ensure that the tip portion 8 is firmly retained in the desired position, spaced from the wall a selected distance at all times. Three fletchings are provided similar to fletching 114, spaced equidistant around the tubing 4.

FIG. 13 also illustrates an embodiment in which the contacting portion 118 terminates prior to the end 120 of the tip portion 8 of the catheter tubing 4. In some embodiments, having the contact location to the blood vessel wall approximately aligned with or slightly behind the actual tip 120 of the tip portion 8 provides advantages in the operation and structure of the device.

FIG. 14 illustrates an alternative embodiment for fletchings 100 illustrating individual fletchings 122, 124 and 126. According to the embodiment of FIG. 14, the fletching 122 extends perpendicular to the catheter tubing 4. That is, the fletching 122 is vertical with respect to the catheter tube 4, like feathers on an arrow. As best shown in FIG. 14, in this embodiment the fletching is formed in a shape which curves quickly upward, and extends in a generally straight, long tapered edge 127 for an extended distance. The thin edge 127 contacts the inter wall 27 of the blood vessel, to anchor the tip portion 8 at a selected position with respect to the blood vessel wall. The fletching has an extended contact edge along the blood vessel wall, to more firmly retain the tubing 4 in a desired angular orientation and prevent rotation of the tubing 4. (This same advantage is provided by selected shapes of the wires of FIGS. 1–9 as well.)

In one embodiment, the fletching 100 is relatively stiff, so as to slightly stretch the blood vessel and at the particular point of contact create a slight depressed channel in which the fletching rests to anchor the catheter. Preferably, the fletching is not so stiff as to penetrate the wall of the blood vessel but, is sufficiently stiff to prevent excessive undesirable rotation of the tip 8. The upper edge 127 may also be tapered to be thinner in cross section than the lower edge 130 if desired, as explained in more detail with respect to FIGS. 18 and 19 herein.

FIGS. 15 and 16 illustrate an alternative embodiment in which the tip retainer 9 is composed of fletchings 132, 134 and 136 very much like the fletchings on an arrow. That is, as explained specifically with respect to fletching 132, the fletching has a long, tapered region 138, a rounded upper region 140 and a rounded end or tip region 142. Just like the fletching on an arrow, the fletching 132 extends vertically away from the tube 4, perpendicular to the catheter tubing 4, similar to the direction of orientation of fletching 122 of FIG. 14.

In the embodiment of FIG. 15, the fletchings 132, 134, and 136 are spaced a selected distance 137 from the end 120 of the tip portion 8. The rounded upper portion 140 contacts the blood vessel wall spaced a selected distance from the tip portion 8, as illustrated in FIG. 15. In the embodiment of FIG. 16, the fletchings 132, 134 and 136 are positioned such that the rounded upper portion 140 is positioned approximately aligned at the end 120.

An advantage of the embodiment of FIG. 15 is that the flow at the catheter end 120 is not obstructed, interfered or altered by the fletchings 132, 134 and 136. Rather, the blood flow is affected only by the presence of the tip portion 8 which can be configured along conventional lines as known in the art to achieve a desired purpose. The contact to the blood vessel walls by the rounded portion 140 is sufficiently close to the tip portion 8 that the tip portion is retained within the blood flow and is prevented from contacting the blood vessel wall.

On the other hand, in the alternative embodiment of FIG. 16, having the rounded portion 140 approximately aligned with the end 120 provides a firm control exactly at the tip 120 to ensure the maintaining of the tip portion 8 at a fixed location within the blood vessel at all times. The end 120 is exactly anchored in position and undergoes little or no movement because the anchor locations around the blood vessel wall are directly aligned with the tip end 120. This provides a firm positioning system for the tip portion a to ensure that the end 120 does not contact the blood vessel wall, even under agitated conditions.

It is contemplated, for example, that in one embodiment a thin wire 139, such as the type shown in FIG. 17A, could be positioned along the tapered edge 138 and along the rounded edge 140 if desired for ensuring that the rounded tip portion 140 always has sufficient spring bias to perform the anchoring function, even in a large blood vessel, and yet have the fletching sufficiently thin for an extended length that it can roll over, providing the improved characteristics of an increased surface contact area if desired.

Figure 17B:
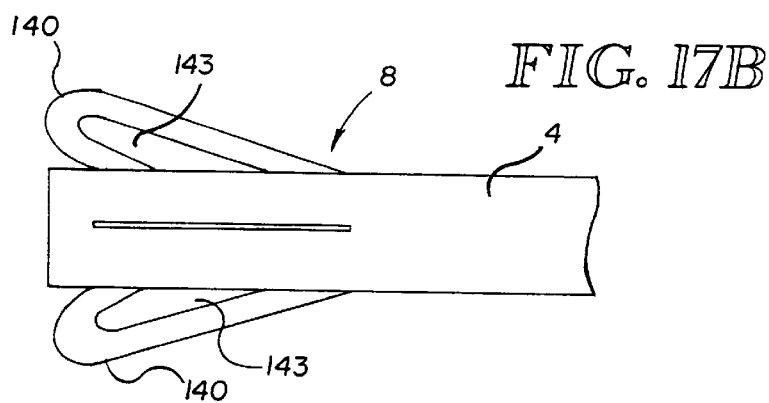
FIG. 17B is a top view of an alternative embodiment of FIG. 17A.

FIG. 17B illustrates a further alternative embodiment for the fletching in which an aperture 143 extends through the fletching. The fletching is thus a ridge of material having a top edge 140. The aperture 143 provides an additional opening for blood flow while the ridges firmly retain the tube 4 within the vessel. The size and shape of the aperture can be varied to alter the spring strength, as desired.

FIGS. 18 and 19 illustrate a particular advantage of the fletching according to the present invention. The fletching is tapered as it extends outward. That is, the fletching is relatively thick at the base 144 where it extends from the tubing 4 and tapers to a very thin edge at the outside regions, particularly at region 140. Having the fletching tapered provides the advantage that one size fletching will fit all blood vessel sizes within a selected range.

For example, as best shown in FIG. 18, the catheter 4 is in a relatively large blood vessel the fletchings 132, 134 and 136 extend straight, and into contact with the blood vessel wall 27. The tip of the fletching 140 may roll over slightly, depending upon the size of the blood vessel. The size of the fletching 132 is selected to ensure that it will at least contact the inner wall 27 of any blood vessel into which it is to be used so that it may perform the tip retaining function as has previously been described. However, in a large blood vessel, such as the type shown in FIG. 18, the tip 140 may slightly contact the edge, thus providing an adequate anchor surface area to retain the catheter tubing 4 in a fixed position as has been described.

FIG. 19 illustrates a smaller blood vessel and the same tip retainer as used in FIG. 18 herein; the fletching is rolled over at the edges, in a broad circumferential contact with the blood vessel wall 27'. The edge 140 can easily roll over and be positioned along the surface of the wall 27' without taking up significant blood vessel area while providing a relatively large contact surface within a small blood vessel. The tapering of the fletching and providing it with thin edges at 140 provides the advantage that even in a small blood vessel, the same fletching may be used except that a larger surface area of the edge portion of the fletching 140 will be in abutting contact with the surface of the wall. This provides the additional advantage of increasing the cross-sectional area of contact between the fletching and the blood vessel, to more securely retain the tip portion 8 within the central region of the blood vessel and prevent contact with the wall 27'.

The tapered fletching provides the additional advantage that a preformed tip assembly 9 can be used in many sizes of blood vessels. A single blood vessel may have a large inner diameter lumen at one region and a small inner diameter lumen in a different region. The difference in diameter may be caused by localized thickening of the walls, injury, fatty build up, or other causes. When the catheter is placed in the vessel, the physician may not be aware of the exact diameter of the blood vessel at the desired location (even though it might be measured ultrasonically, for example). The physician is assured that the catheter tip will be properly retained in the blood flow and spaced from the wall even if the exact dimensions are not as was expected at the installation site. (This advantage is provided in other embodiments also, such as the embodiments of FIGS. 1–9 by the selective withdrawal or extension of the wires, as previously explained.) Having tapered edges provides another distinct advantage: the relative flexibility and spring bias within the fletching may be easily altered along the fletching as it extends outward. That is, at the very edge of the fletching near rounded portion 140, the resilient bias can be very light because the fletching is very thin at the edges. Closer to the base, the fletching gradually becomes thicker, naturally increasing the spring strength and resilient bias within the fletching. This has the advantage of increasing the centering ability of the tubing 4 because if the tubing begins to be pressed out of position, towards one wall the fletching on that side of the tubing will have the base region pressed closer to the wall; however, the base region being thicker and having a stronger spring action will tend to increase the resilient bias away from the wall to push with more force away from the wall and tend to center the tubing 4 within the blood vessel. Each of the fletchings are constructed with uniform spring bias to act together in generally centering the tubing 4 within the blood vessel and prevent the tubing from becoming too close to the blood vessel wall on any side.

In one embodiment, the spring strength of the fletching varies proportional to the thickness of the fletching. In an alternative embodiment, the fletching is constructed such that the spring bias is not uniform with respect to the thickness of the fletching. For example, a relatively strong spring bias can be placed adjacent the base, even more than would otherwise be present, to ensure that the tubing 4 is always spaced at least a minimum distance from the wall 27. Alternatively, a slightly stronger spring bias may be placed right at the tip 140 than would otherwise be present based on the edges being extremely thin because the edges may be so thin as to have little or no spring bias based on their own thickness. In such an embodiment, the properties of the material or the type of material used may be slightly altered at the very tip region 140 to provide sufficient spring strength to anchor the end even though the tip portions are extremely thin.

FIGS. 18–21 also illustrate alternative embodiments for the orientation of the fletching on the tubing 4. According to one alternative embodiment as shown in FIGS. 18 and 19, the fletching is straight, directly in line with the tubing 4. This is the same style for mounting the fletching on some arrows, as is known in the prior art. Alternatively, the fletching may be mounted at a cant to provide a spiraled fletching as best shown in FIGS. 20 and 21. When the fletching is mounted at a cant, so as to slightly spiral around the tubing 4 this provides the advantageous effect of smoother blood flow through the blood vessel while aiding to maintain the tip 4 in a straight-line orientation with respect to the blood vessel.

The fletching as illustrated in FIGS. 12–21 has the advantage of being easily constructed. In one embodiment, the molding 4 and fletching is constructed as an integral piece by injection molding methods known in the art. The material can be constructed from a polymer, silicone, or any other well-known nonthrombogenic material. Alternatively, the tubing 4 can be extruded with the fletching being provided in an extrusion mold process. Another advantage of the fletching is that it permits easy sheath removal and insertion, as will be explained later in more detail. The fletching also is easily constructed with graduated stiffness along the length of the fletching as it extends away from the tubing 4 providing the advantages previously described.

The insertion and removal of the catheter tubing 4 having the tip retainer on the end thereof will now be explained in particular detail with respect to FIGS. 22–24. The description of FIGS. 22–24 is particularly directed towards an embodiment having loops generally of the type previously described with respect to FIG. 9; however, this is for illustration purposes only and the same or similar method of insertion and removal is uniformly applicable to each of the embodiments described herein.

Referring now to FIG. 22, the catheter 4 having the tip retainer 9 at the end thereof is prepared for introduction into the blood vessel by placing it within an introducer sheath 148. The introducer sheath 148 is preferably made of polyurethane, plastic or some other relatively pliable material that is sufficiently stiff to overcome the spring bias of the retainer member so that the entire assembly has a diameter approximately equal to that of the catheter tubing 4. The introducer sheath 148 includes a handle portion 150 which the physician may use to manipulate the introducer sheath 148 and guide it into the proper position within the blood vessel. In a preferred embodiment, the introducer sheath 148 has a slight taper 152 at the distal end to make the introduction into the blood vessel more simple.

As shown in FIG. 23, the introducer sheath is advanced into the blood vessel 30 until the catheter tube is at the desired location within the blood vessel. At this position, the tip retainer 9 is held within the introducer sheath and does not contact the wall of the blood vessel 30.

As shown in FIG. 24, the introducer sheath 148 is then removed from the catheter tubing 4. According to a preferred embodiment, the introducer sheath 148 is constructed of a relatively thin layer of polyurethane which is easily ripped or torn by the physician. In order to remove the introducer sheath, the physician firmly grabs the handles 150 on either side and begins to tear apart the introducer sheath. The introducer sheath will separate into two pieces, tearing apart outside of the blood vessel and withdrawing the introducer sheath from the catheter tubing 4. As the introducer sheath is withdrawn from the catheter tubing 4, the tip retainer is released and automatically extends outward according to the preset spring bias to contact the blood vessel wall and retain the tip portion 8 at the selected location as has been previously described.

In an alternative embodiment, the sheath is simply removed by sliding it backwards, rather than tearing the sheath into two pieces. As will be appreciated, tearing the sheath into two separate pieces provides the distinct advantage of permitting the introducer sheath to be easily separated from a portion of the tubing without having to completely slide off the end of the tubing outside the body. It also provides the advantage that the physician may easily and uniformly withdraw the introducer sheath while leaving the tubing 4 in the preset position, to permit the tip retainer to be deployed to retain the tip portion 8 in the desired position within the blood vessel.

Removal of the catheter 4 having the tip retainer 9 on the end thereof is easily accomplished with each of the alternative embodiments. In the alternative embodiments of FIGS. 5–21, it will be appreciated that the tip retainer does not penetrate the blood vessel wall 27. Further, in many of these embodiments the tip retainer is constructed to permit easy withdrawal or removal from the blood vessel. According to one method of removal, the catheter 4 is simply withdrawn from the blood vessel, and simultaneously withdraws the tip retainer while in the deployed position. Even though the tip retainer is deployed, such is shown in FIGS. 8 and 9 and others, the orientation is such that the withdrawal may be easily accomplished because the spring bias permits the tip retainer 9 to be pressed inward slightly as necessary. To advance the tip retainer would be difficult, or impossible, because this would serve to increase the spring bias and press the tip retainer 9 more firmly into position against the blood vessel wall, increasing the anchor strength. On the other hand, the withdrawal of the catheter tube 4 tends to pull the tip retainer 9 away from the wall and permit easy removal without excessive stress on the blood vessel wall.

According to an alternative embodiment, the tip retainer is withdrawn from the deployed position so as to not contact the wall by sliding an introducer sheath once more over the tip portion 8 to withdraw the tip retainer 9 from the blood vessel wall. The sheath and catheter tube 4 may then be withdrawn from the blood vessel.

A large number of tests have actually been conducted regarding particular alternative embodiments of the invention. By way of example, and not to limit the scope of the invention, the salient alternative embodiments will now be more particularly described with respect to FIGS. 25–85.

FIGS. 25–36 illustrate a further embodiment of the catheter having a tip retainer 9 of the type described herein. In the embodiment shown in FIGS. 25–36, the tip retainer 9 is extended or retracted by actuating a single wire 184 which extends through a longitudinal guideway 172 along the full length lengthwise dimension of the catheter 4. At the proximal end of the catheter 4 is an actuating mechanism such as knob 170 and hub 143. The combination thereof operates to retract and extend the wire 184 and the tip retainer assembly 9, as explained in more detail hereinafter.

The hub 143 is preferably constructed of a rigid plastic and is attached to the proximal end of the catheter 4. The knob 170 is also composed of a rigid plastic or other firm material. Connected to the knob 170 is a single wire 184. A cable sheath 186 is carried inside the guideway 172. Preferably, the sheath 186 is rigidly and fixedly attached at its two ends, to the hub 143 and the distal end 8. For example, FIGS. 33–36 show the proximal end of the cable sheath 186 attached to the guideway with an adhesive 173. The sheath 186 may move freely within the guideway 172 as shown in FIG. 27, in which the sheath is spaced from guideway 172. The sheath 186 is preferably a Teflon™ sheath, or other low friction sheath material. The wire 184 and sheath 186 combination form a cable combination, with the wire 184 being the wire inside the cable assembly. The sheath 186 is held stationary with respect to hub 143 while the wire 184 is retracted or extended and the sheath provides the tension necessary to permit the wire 184 to be extended or retracted as necessary. This type of sheath/wire assembly generally known in the field of brakes for bicycles, and other mechanisms controlled by wires.

The wire 184 is, in one alternative embodiment, coated with a thin layer of Teflon™ or other lubricious material to increase the low friction sliding nature between the stationary sheath 186 and the internal wire 184. As best shown in FIG. 36, when the guideway 172 and sheath 186 reach the distal tip 8 of the catheter 4, they are enlarged to provide an open cavern area from which additional shorter guideways and sheaths may extend. Specifically, the large cavern area 174 is preferably formed of a cable sheath material which encompasses the entire joint area and has exiting from it small guideways 175, 176, 178, and 180 in the embodiment in which four individual ends of wires 194–197, respectively, are connected to the single wire 184. The external surface of the sheath in the cavern area 174 preferably includes an adhesive thereon to retain the sheath 186 in the cavern area 174. If fewer or more wires are connected, fewer or more corresponding guideways are provided as necessary so that each wire has an individual guideway and sheath near the distal end 8. The guideways 175, 176, 178, 180 extend from the enlarged cavern area 174 to the distal end or portion of the catheter 4 as desired. The guideways extend circumferentially around the outer diameter of the catheter 4 to the desired location to provide exit holes spaced as desired, as best shown in FIGS. 30 and 36. Specifically, the guideway 178 extends generally straightforwardly from large cavern 174 to the opening at the end 120. The guideway 180 spirals a short distance around the catheter 4 to extend to the desired location, shown in FIG. 30. The guideway 175 extends in a spiral radially around the catheter 4 as well as the guideway 176, to the desired locations shown in FIG. 30.

The enlarged cavern 174 provides an enlarged area to permit movement of the wire 184. Specifically, the junction 177 (shown in FIG. 36) is where the wires 194–197 that run in guideways 175, 176, 178 and 180 connect to the wire 184. An enlarged cavern is required along the junction 177 to allow the wire to move back and forth a short distance at the intersection of the longitudinal wire 184 and the short wires 194–197. The wires 194–197 that run in the guideways 175, 176, 178 and 180 wrap around the tip of the catheter to exit at their desired location, depending on the design of the catheter and the intended location of placement of the distal end thereof.

In this embodiment, the distal tip cavern 174 and guideways 175, 176, 178 and 180 may be preferably coated or lined with a lubricous or slippery material, such as a Teflon™-based material, to facilitate the movement of the wire within the cavern and guideways to provide a low friction surface therebetween. Additionally, as shown in FIGS. 27–30, the wires in the guideways 175, 176, 178 and 180 may be a sheath/wire. combination similar to that shown and described with respect to wire 184 in sheath 186 within guideway 172.

The use of a single wire along the lengthwise dimension of the catheter allows the catheter to be bent without significantly affecting the relative distance each of the loops extends from the tip 8 of the catheter. For example, if the catheter as described above with respect to FIG. 1 were bent during insertion, one or more of the wires would be positioned near the outer surface of the curve while one or more of the other wires would be positioned near the inner surface of the curve. If this difference in length along the inner surface of the curve as compared to the distance along the outer surface of the curve is not accounted for by adjusting the wires along the length of the catheter in the embodiments where the wires extend the length of the catheter, the wires and loops (if used) will extend from the tip of the catheter at varying distances and the tip may be positioned closer to one surface of the blood vessel than another. (In the embodiment of FIGS. 1–7, the physician may elect to vary the length of the individual wires and therefore, may approximate the differences in length by adjusting the individual wires.) With the present embodiment, the distance each wire or loop extends from the tip will be affected equally by the curvature of the inserted catheter because the curvature will occur along the portion of the catheter which includes the single wire therein.

As shown in FIGS. 32–35, the proximal end of the catheter 4 of this embodiment a mechanism to conveniently extend or retract one or more wires of the catheter. This embodiment includes a hub portion 143 fixed on the catheter 4, and a knob 170 which is attached to the hub. The knob includes a hole 188 having the proximal end of the wire 184 retained therein. A bulbous transition area 192 is formed in the hub portion 143 distally of the knob 170 and along the lengthwise dimension of the catheter to accommodate the wire 184 therein as the knob 170 is rotated to move the wire 184 distally or proximally in the longitudinal guideway 172. When the user desires to extend the wires or loops that comprise the retaining assembly 9, the knob 170 may be rotated clockwise to cause the wire 184 to contact the lower, curved surface of the bulbous guideway 192. The bulbous area 192 provides a smooth transition area to permit the rotational motion of the knob 170 to be transferred into longitudinal movement of the wire 184, as best shown in FIG. 35. That is, as the knob 170 is rotated, the wire 184 contacts the lower surface of the bulbous portion 192 in the hub portion 143 to provide a smooth transition region to transfer the rotational movement of the wire on the knob into the longitudinal movement of the wire 184 in the longitudinal guideway 172 to extend the wire or loops which comprise the tip retainer 9. According to one aspect of the invention, a desirable feature of this embodiment is that the wire is fed smoothly along the bulbous part of the guideway 172 to provide a low-friction, smooth transition into longitudinal extending motion. The guideway 172 can be Teflon™ coated as desired, to provide a low-friction surface. In a preferred embodiment, the edge of the hole 188 is curved along a bottom surface to permit an easy exit of the wire 184 into the bulbous area 192 upon extension. In this embodiment, the edge 193 on the hub portion of the catheter above the bulbous edge 192 is a square corner which provides a sharp turn in the wire. Alternately, the upper surface may have a curved surface, to permit a smoother transition into the bulbous area of the wire so that a distinct 90° turn of the wire is not required. This serves to facilitate the smooth extension of the wire upon rotation of the knob 170.

The knob 170 includes at the proximal end, a groove 182 as best shown in FIGS. 26 and 31. The groove 182 extends around a wall surface on the distal end of the knob 170 and provides an opening into which the wire is laid as the knob is rotated. Alternately, the groove 182 may be on the proximal end surface of the hub 143. Specifically, when the user desires to retract the wire on loops, they rotate the knob counterclockwise to wrap the wire 184 into the groove 182 between the knob 170 and hub 143. The tolerance between the knob 170 and the end of the hub 143 may be made extremely tight because of the groove 182. Specifically, as the wire is retracting, it can feed into the groove and does not require an increase or decrease in the distance between the hub 143 and the knob 170. Because the distance between the retracted and extended positions of the wires or loops is relatively small, it is not necessary to rotate the knob multiple revolutions around the catheter in order to effect the desired result of extending or retracting the wire or loops on the tip. Although the present embodiment is shown with a knob that is rotatable with respect to the catheter, it is anticipated that nearly any other type of actuation may be used to retract and/or extend the multiple members along the tip of the catheter from a preferably single wire.

Figure 73:
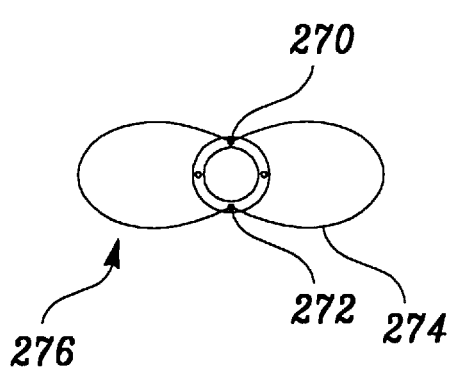
FIG. 73 is an end view of a further alternate embodiment of the present invention.

As shown in FIG. 36, the distal end portion of the catheter 4 includes a plurality of relatively short guideways 175, 176, 178 and 180 thereon which project radially along the tip portion 8 of the catheter 4 from the distal end of the longitudinal guideway 172. This embodiment illustrates the use of four wires that comprise two loops 274 and 276 which project radially outwardly from the tip such as shown in FIG. 73. Each wire is positioned in a separate guideway which runs along the tip 8 of the catheter 4 between the cavern area 174 and four preferably equally spaced-apart openings on the tip 8 of the catheter. The length of each wire is determined by the distance between the junction 177 and the opening for the specific wire so that, as shown in FIG. 36, each wire will have slightly different length. Alternately, the loops 274 and 276 may be replaced with individual wires as described above or below.

Figure 37:
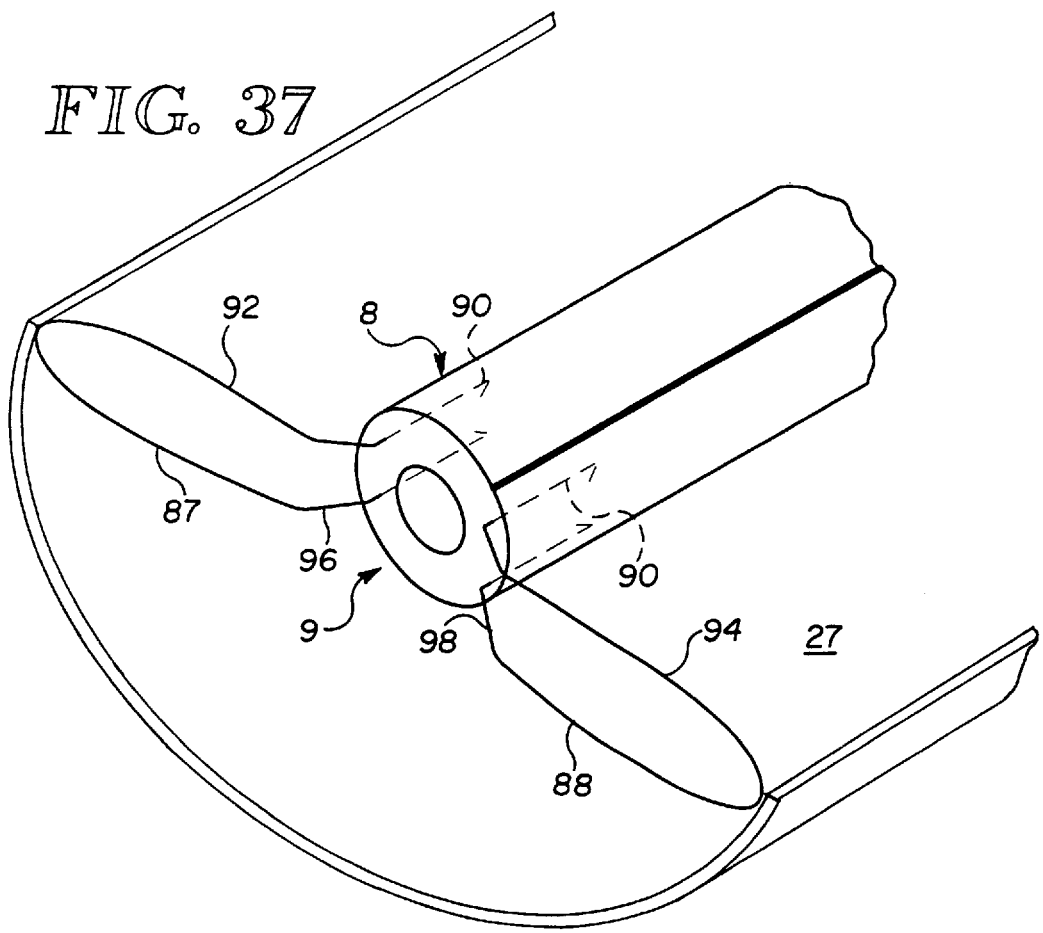
Figure 38:
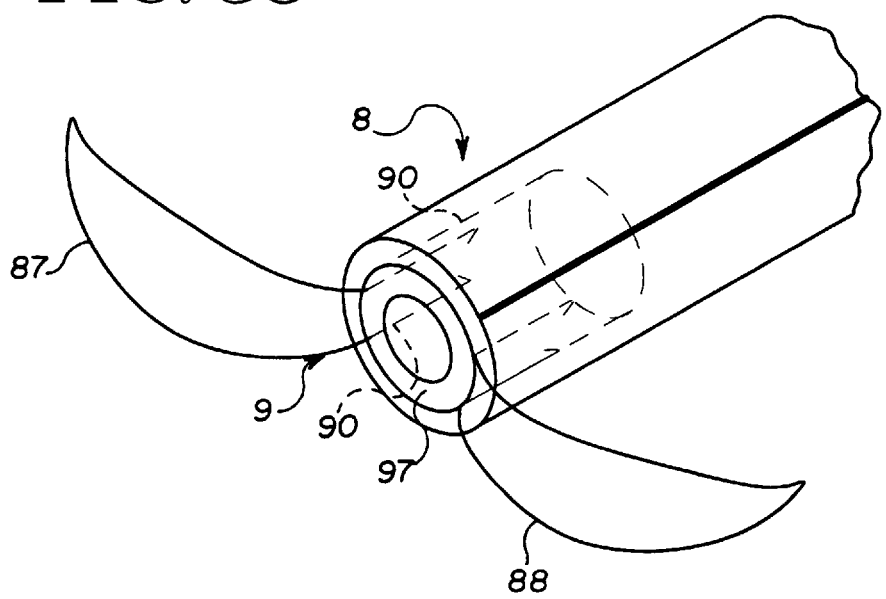

FIGS. 37 and 38 illustrate an embodiment that forms two loops using only two wires 87 and 88. Different from the previous embodiments of FIGS. 8 and 9, the two wires 87 and 88 of FIGS. 37 and 38 are relatively short wires which are firmly embedded in the tip 8 of the catheter. The wire 87 has one end 90 embedded in the tip, as shown in dotted lines, and then extends in a loop out of the tip 8 and then returns and has the other end 90 embedded at a different location within the tip 8. Wire 88 is similarly attached to the tip. The wires 87 and 88 form loops that may be rounded (FIG. 37), or a cloverleaf pattern as in FIG. 8 but having only two wires, forming two loops, rather than four loops with eight wires.

According to this preferred alternate embodiment of the invention, only two loops formed of two wires are used to anchor or secure the catheter tip 8 with respect to the blood vessel wall and firmly retain it within the blood flow so as not to contact the wall 27. The large loops provide an increased surface contact area with the blood vessel such that two wires with the larger loops are sufficient to retain the tip 8 within the bloodstream flow so as not to contact the wall 27. In preliminary testing, a gentle, easy-bend loop has been found useful for retaining the catheter 4 in the blood vessel. (The blood vessel 30 shown in FIG. 37 is illustrated somewhat larger than the anticipated size where the catheter tip is actually positioned to more clearly illustrate the loops 87 and 88; in practice, the tip region 8 would likely be in a smaller diameter portion of the blood vessel and the loops 87 and 88 somewhat deflected by large area contact with the wall 27.)

Having the loops 87 and 88 anchored in the tip region 8 provides significant advantages in the manufacturability, cost and operation of the inventive tip retainer. The loops 87 and 88 can easily be attached to the tip portion 8 by numerous techniques. One technique is embedding the wires into the tip material itself after the tip has been constructed with the bent end 90 acting as a fishhook to retain the end within the tip 8, as shown in FIG. 37.

Another technique as illustrated in FIG. 38 is to retain the wires 87 and 88 against a cylinder 97. The ends 90 are held against the cylinder 97 and then the cylinder 97 is inserted into the lumen on the distal end of the catheter. The ends 90 are held by being pressed between the outside cylinder 97 and the inside wall of the catheter lumen. In one embodiment, the cylinder 97 is formed of a slightly harder or firmer material than the catheter itself, providing the additional advantage that the lumen is held open more firmly at the tip of the catheter. For an extruded catheter, the wires may be placed into the catheter assembly as it is extruded or shortly thereafter.

The embodiments of FIGS. 37 and 38 provide a relatively simple method of operation because the user need not be concerned about moving or positioning the wires. Although it is advantageous during some uses of the device of the present invention to be able to manipulate the wires as shown for the embodiments of FIGS. 7, 8 and 9 of FIGS. 25–36, there are other uses of the present invention in which the simplicity obtained by having the wires automatically preset and prestressed to bend with the desired flex outward to contact the walls is useful.

As described above, FIG. 37 illustrates an alternative embodiment for the tip retainer 9 being formed of two loops of wire 87 and 88, respectively. The wires 87 and 88 of this embodiment have a "gull wing" configuration in which the loops have a straight portion 96 and 98, respectively, which is angled outwardly from the catheter and a looped portion 92 and 94, respectively, adjacent to the straight portions 96 and 98, respectively.

The gull wing shape as shown in FIG. 37 for the tip retainer 9 provides the advantage of a broad, longitudinally extending contact surface between the wires 87 and 88 and the blood vessel wall. The longitudinal extending contact surface is advantageous in some embodiments for ensuring firm contact along an extended length in the direction of the blood vessel to firmly anchor or secure the tip 8 with respect to the wall and maintain the distal end of the catheter spaced apart from the wall within the fluid flow. The wires 87 and 88 are preferably anchored into the tip 8 as shown in FIG. 37.

Similarly, the angle of connection between the straight portion 96 and the loop portion 92 can also be selected as desired. Thus, in the gull wing configuration, the bias force extending outward is easily selected or adjusted according to the desired use of the catheter.

Figure 39A:
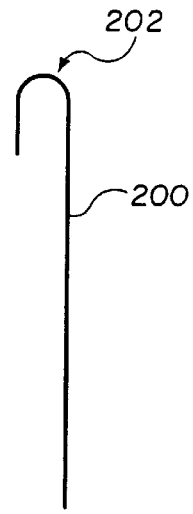

As shown in FIG. 39A, a wire 200 for use with the tip retainer 9 is formed having a hook portion 202 at one end thereof. The wire 200 corresponds, alternatively, to the wire 12, the wire 72, or numerous other wires which have been described in the alternative embodiments above and to be described in the following alternative embodiments. The hook 202 corresponds to the hook 90 of FIGS. 38 and 37 and preferably includes a hook portion which is about 1.7 to 2.0 mm long for a wire 200 which is about 10 or 11 mm long.

According to one alternative embodiment, the wire 200 is a stainless steel wire about 0.01 inch in diameter and ranging in length from 13 to 20 mm for those embodiments using a straight wire, such as those illustrated in FIGS. 1–6. For wires which are formed into a loop, such as shown in FIGS. 37 and 38, the wire 200 may have a preferred length in the range of about 16 to 60 mm. Uncoated stainless steel can be used, or, alternatively, the stainless steel can be coated with an antithrombogenic coating, as previously discussed.

Any suitable catheter tubing can be used. One catheter tubing which has been found acceptable is that sold by Quinton Instrument Company of Seattle, Wash., U.S.A., as a single-lumen tubing of 5.1 mm in diameter made of silicone. A dual lumen tube is also suitable.

According to one embodiment of the present invention, the hook 202 is formed by placing the wire 200 in the appropriate holder, which, in one embodiment, is inside the shaft of a blunt needle. Alternatively, forceps, pliers, or other tooling may be used to form the hook 202. Holes are cut in the end of the catheter tubing 4 and the bent hook portion 202 is inserted into the cut in the tubing so that the hook portion 202 will prevent the removal of the wire 200 therefrom.

Figure 39B:
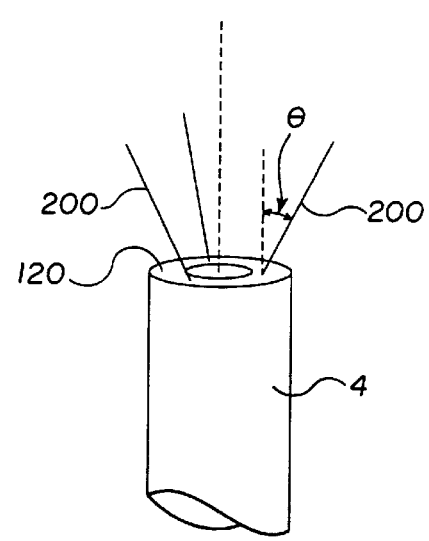

As shown in the embodiment of FIG. 39B, three or more wires are inserted, equidistant from each other, into the end of the tubing. Care is taken to ensure that the wires 200 do not pierce either the inside or outside wall of the tubing. An attempt is also made to not create bumps in the sides of the tubing so that it remains as smooth as possible.

FIG. 39B illustrates an angle θ at which the wires are mounted and retained inside the distal end face 120 of the tubing 4. The angle θ is selected based on the intended use of the catheter. If the catheter is being inserted into a lumen only slightly larger than the catheter itself, the angle θ will necessarily be small, possibly in the range of 10° to 20 degrees. However, if the catheter is inserted into a lumen which is significantly larger in diameter than the catheter, for example, 3 to 4 times the diameter of the catheter, the angle will be correspondingly larger. For example, the angle may be in the range of 20 to 45 degrees, depending upon the diameter of the blood vessel into which the catheter is intended to be inserted and the length of the wire. As will be appreciated, for a shorter wire in the same diameter blood vessel, the angle must be correspondingly larger in order for each of the wires to properly contact the interior wall 27 of the blood vessel. Preferably, the angle θ is equal for each of the individual wires so that the catheter 4 is retained exactly in the center of the blood vessel 30. The method of angle construction which has just been described for FIGS. 39A and 39B is also applicable to the tip retainer 9 of the type shown in FIG. 4.

Figure 39C:
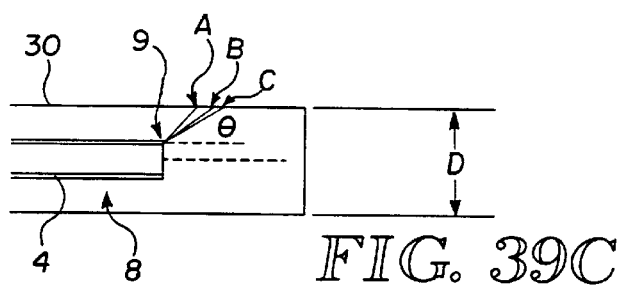
Figure 39D:
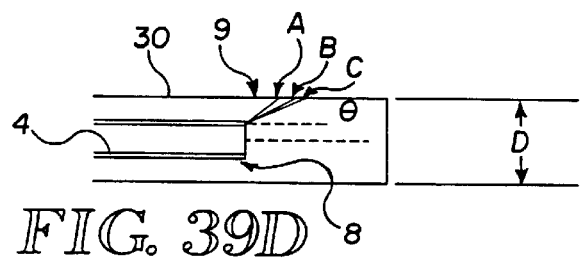

FIGS. 39C and 39D illustrate, by way of example, the actual wire lengths and angles which may be used for deployment. In the example shown, the size of the blood vessel may be in the range of 18 mm in diameter. In another embodiment, the size may be in the range of 15 mm in diameter. With this in mind, the length of the wire from the end of the tubing and the wire bend angle are both changed so that the wire appropriately contacts the side of the tubing wall. For example, with an 18 mm diameter blood vessel shown in FIG. 39C as D, the relative wire length and angles may be 10 mm at 44.7° (A); 12 mm at 36.5° (B); or 14 mm at 30.7° (C). For a 15 mm diameter blood vessel shown in FIG. 39D as D, the wire length and angles may be 10 mm at 33.4° (A); 12 mm at 28.1° (B); or 14 mm at 23.8° (C). While these angle changes in response to varied wire length are described with respect to the straight wires 200 generally as shown in FIG. 39B, similar changes in the angle and the loops will be made for each of the embodiments of FIGS. 1–85, as appropriate depending on the intended use of the catheter and numerous other considerations.

Figure 40:
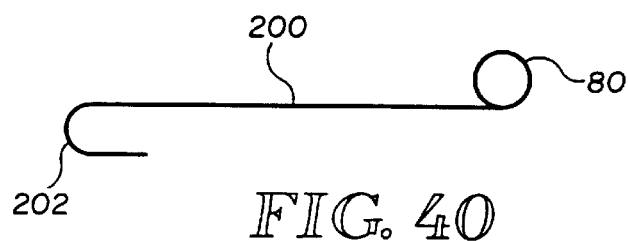

FIG. 40 illustrates an alternate construction of the wires for a tip retainer 9 similar to the type shown in FIG. 39A. The wire 200 has a loop 80 formed at one end thereof and a hook 202 at the other end thereof. The plane of the hook and the plane of the loop are preferably perpendicular to each other. The wire 200 of FIG. 40 is inserted into the end 120 of the tube 4 in the same manner as described above and provides the advantages previously described with respect to FIGS. 37 and 38.

As will be appreciated, the wires used for the retainer assembly can be any acceptable wire or line, including stainless steel wire, spring wire, guitar wire, a stiff monofilament line, or the like. Further, the wire can be used as bare wires, silver coated wires, Teflon™-coated wires, wires coated in a silicon dispersion, or any other acceptable coating which will not create a reaction inside the blood vessel of a living animal.

Figure 41:
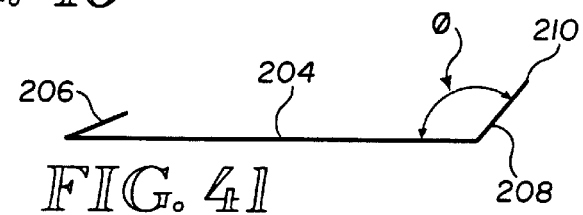
Figure 42:
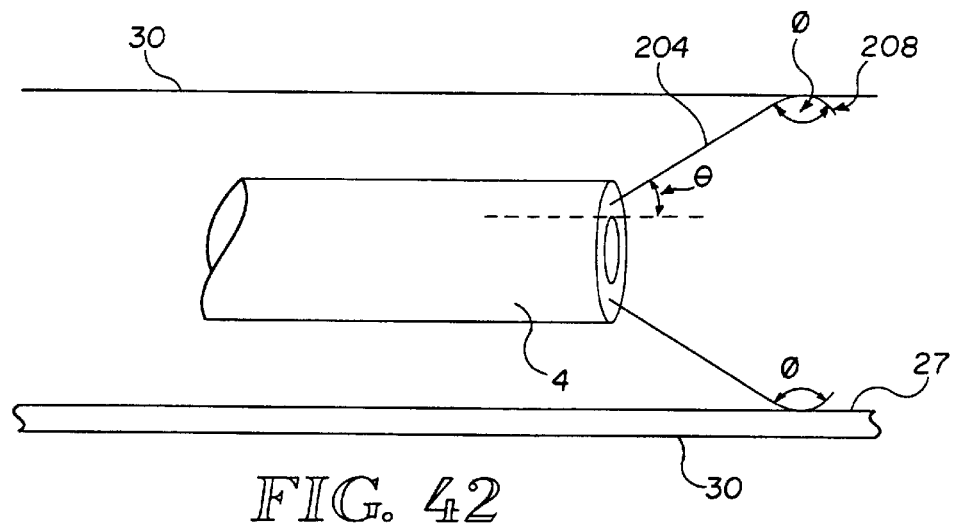

FIGS. 41 and 42 illustrate an alternative embodiment for the shape of the wire 204. Particularly, the wire 204 has a sloped region 208 bent at an angle φ with respect to the straight portion 204. The other end of wire 204 contains a hook 206, formed in the manner previously described or by a sharp bend in the wire, such as may be made with forceps or pliers. The plane of the sloped portion 208 is generally perpendicular to the plane of the hook portion 206. Preferably, the length of the sloped portion 208 is approximately 2 to 3 mm and the angle φ in the range of 120 to 140 degrees. In one embodiment, an angle of 135 degrees has been found acceptable. Four wires 204, configured as shown in FIGS. 41 and 42, are inserted into the distal end face 120 of the catheter tubing 4 and bent at an angle acceptable for the intended use to provide a catheter of the type shown in FIG. 42. In one embodiment, an angle φ of 28 degrees has been found acceptable.

The angle φ is selected to ensure that the bent portion 208 lies along the wall of the blood vessel to increase the surface contact area. Alternatively, the angle φ is selected to ensure that the bent portion 208 points slightly inward, in the event that the blood vessel has a greater diameter than anticipated, to ensure that the tip 210 of the bent portion 208 does not penetrate the wall but rather points either parallel to the blood vessel wall or slightly inward, as shown in FIG. 42.

Figure 43:
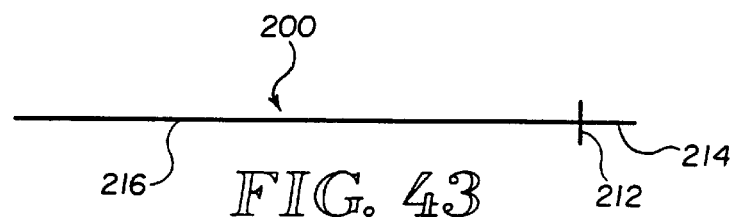
Figure 45:
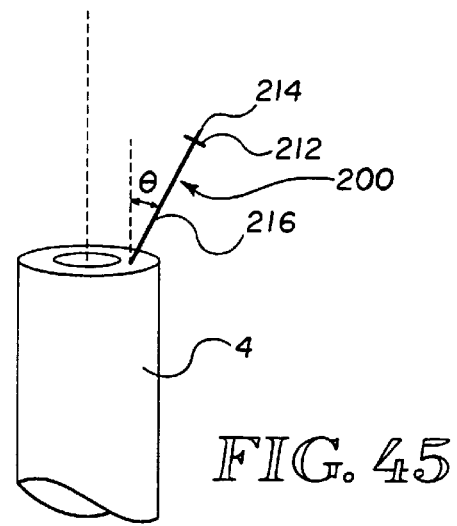

FIGS. 43 and 45 illustrate a wire 200 having a foot 212 thereon and a vessel wire 214 extending beyond the end of the foot 212. The wire 200 can be plastic, ceramic, metal or other similar materials. The straight portion of the wire 216 ends in a hook, as previously described, the hook not being shown in FIG. 43. Preferably, the foot 212 has a foot area of approximately 1 mm in diameter which will contact the sides of the vessel wall. The vessel wire 214 will also contact the blood vessel wall and, in some embodiments, will actually go into the side of the blood vessel wall by penetrating it. The foot 212 can be constructed of any acceptable material that does not cause an adverse reaction in the body and prevents the tip 214 from penetrating beyond a described depth into the wall. For example, an absorbable suture material, coated stainless steel, a polyglycolic acid, PGA, or the like. Alternatively the foot 212 may be in the form of a weld bead or solder bead that prevents the tip from penetrating too deep into the wall.

Figure 44:
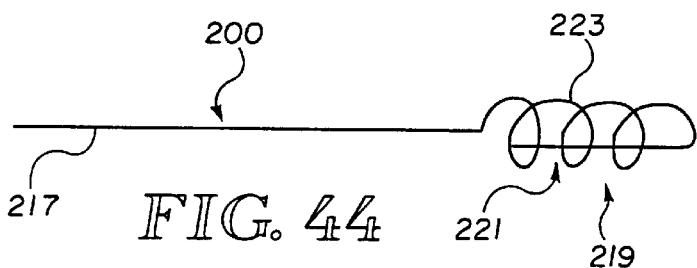

FIG. 44 illustrates a further alternative embodiment for the wire 200 of the tip retainer assembly 9. According to this alternative embodiment, a straight wire 217 has a plurality of loops 219 formed at the distal end thereof. The loops 219 can be formed by any suitable method, including wrapping the wire around a solid core or other acceptable method so as to form the coil 219, similar to that of a spring. The tip 221 is curved over itself and extends within the loops 219. Having the tip 221 pointing backwards, and positioned within the loops 219 protects the walls of the blood vessel to ensure that the tip 221 does not penetrate the blood vessel wall. When the wire 217 is deployed, the proximal end is inserted into the catheter 4 in a manner similar to that described above with respect to the prior embodiments. The wire 217 is positioned in the catheter so that the outside portion of the loops 223 is in contact with the blood vessel wall.

FIG. 45 illustrates one embodiment for the mounting of the wire 216 shown in FIG. 43. The angle θ of the embodiment shown in FIG. 45 is preferably in the range of about 0 to 90 degrees. This angle θ is selected such that one side of the foot 212 contacts the wall and the vessel wire 214 contacts the wall near the tip, or may actually slightly penetrate the wall. The ends of both the foot 212 and the vessel wire 214 preferably contact the wall, thus forming a stable bridge which will spring-bias the tubing 4 into the central region of the blood vessel, either three or four wires 216 are preferably used in the embodiment of FIG. 45.

FIG. 46 illustrates an alternative embodiment for the wire 200 shown in FIG. 43. In the embodiment of FIG. 46, the straight portion 216 is bent outward so that the shape of the wire 216 forms a curve with the wire foot 212 oriented parallel to the vessel wall, with the other end of the wire inserted into the face 120 of the tube 4 in a manner previously described. Four wires are inserted equidistant from each other into the end 120 of the silicone tubing. In an example of the present alternate embodiment, the wire length from the end of the catheter tube to the end of the wire is approximately 15 mm and the distance from the center one foot 212 to the center of the other foot 212 on the opposite side of the tubing is in the range of 20 mm. As set forth above, the lengths are for example only and will be selected depending on the intended use, type of catheter and many other variables known to those in the art. The tip retainer 9 is mounted on the tubing 4 and placed inside the blood vessel, with the vessel wire 214 penetrating the blood vessel wall similar to the prong 26 previously described and the foot 212 limits the amount the wire is able to penetrate into the blood vessel.

FIGS. 47 and 48 illustrate a further. alternative embodiment according to principles of the invention. As shown in FIG. 47, a hook 202 is formed in each end of a wire 200, the wire having a preferred length in the range of 20 to 50 cm, depending upon the end use thereof. The wire 200 is then shaped to form the loop 218, as shown in FIG. 48. The ends 202 are then inserted into the distal end face 120 of the catheter tube 4.

FIG. 49 illustrates a further alternative embodiment according to the invention in which stainless steel stepwires 220 are used. For the sake of clarity, only two stepwires 220 are shown while the preferred form of this embodiment uses four equidistant wires. The stainless steel stepwire is a single wire having two diameters, a thick diameter portion 222 and a thin diameter portion 224. The small diameter portion 224 of the wire is sufficiently small that it can easily penetrate the wall of the blood vessel. The larger diameter portion 222 of the wire is sufficiently large in diameter that it acts to prevent the wire from penetrating deeper into the blood vessel wall than the length of the small diameter portion 224. According to one embodiment, the small diameter wire is about 0.003 inch in diameter and has a length of 1 mm, and the large diameter wire has a diameter of about 0.007 inch or nearly twice the diameter of the small diameter portion.

FIGS. 50 and 51 illustrate an alternative design along the same lines as the foot wire designs of FIGS. 43, 45 and 46. For the sake of clarity, FIG. 51 shows only two wires 200 while the preferred form of the present embodiment includes four equidistant wires 200 thereon. According to the alternative design of FIGS. 50–51, the wire 200 is bent to place a small loop 226 near the distal end thereof. The small loop 226 acts as a foot to prevent the vessel wire 228 from penetrating beyond a desired depth into blood vessel wall. The shape of the wire is such that it forms a curve so that the loop 226 is parallel to the vessel wall when the other end 230 is inserted into the silicone tubing 4, as diagrammatically shown in FIG. 51. As previously described, a hook (not shown) is formed in the end 230 of the wire so that it will penetrate solidly and be held in the silicone tubing. Four wires are preferably inserted equidistant from each other into the end of the silicone tubing.

Figure 52:
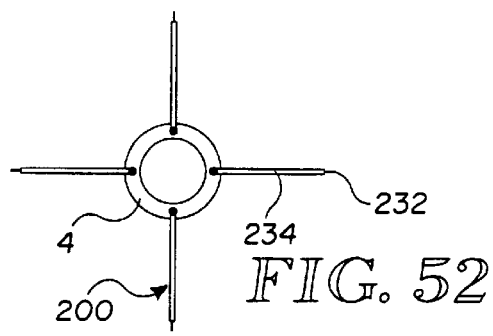
Figure 53:
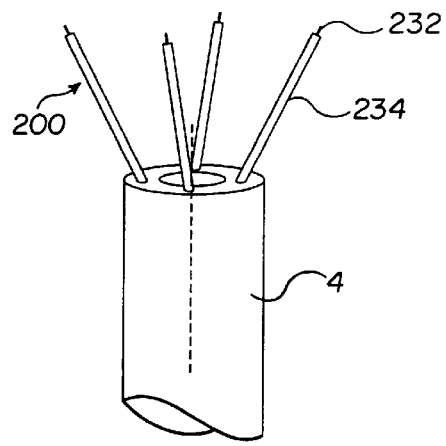

FIGS. 52 and 53 illustrate a further alternative embodiment according to the present invention. The wire 200 is inserted into the distal end face 120 of the tube 4, as previously described. Each wire 200 is then covered with a piece of Teflon™ tubing. The Teflon™ tubing is inserted a desired depth into the catheter tubing 4 to retain it in position. A small tip portion 232 extends beyond the end of the Teflon™ tubing 234. The wires 200 are then bent at an angle to contact the blood vessel wall at the desired position, as previously described. In one example of the embodiment, the tip portion 232 was about 2 mm long while the Teflon™ tubing 234 was about 15 mm.

Figure 54:
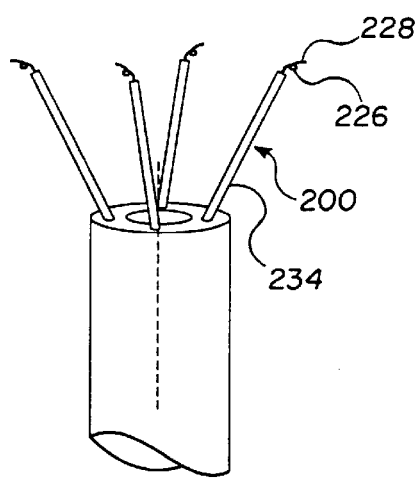

FIG. 54 illustrates an alternative embodiment to FIGS. 52 and 53. Specifically, a loop 226 is placed in the wire 200 just beyond the Teflon™ tubing 234, and the vessel wire portion 228 is bent, as previously described, to penetrate the wall of the blood vessel.

Figure 55:
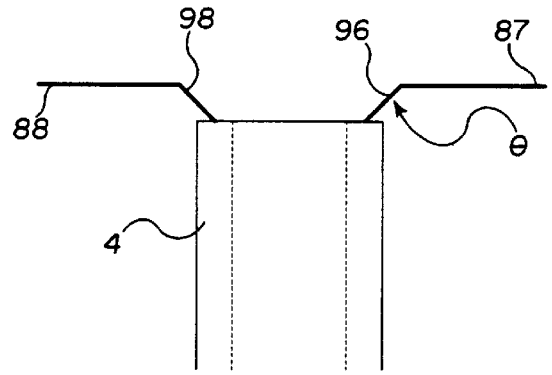

FIG. 55 illustrates a side view of an alternate embodiment similar to FIG. 37, having the gull wing configuration. According to this embodiment, the straight portions 98 and 96 extend from the tubing 4 with such an angle θ that the loops 87 and 88 extend substantially perpendicular to the walls of the tubing 4. In one embodiment, the straight portions have a length in the range of 3 to 4 mm, such that the height distance from the loop 87 to the distal end surface 120 of the tubing is in the range of 1 to 2 mm although the respective lengths and relationships of the various members will vary depending on the relationship between the respective elements.

Figure 56:
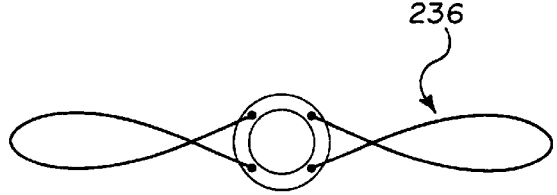

FIG. 56 illustrates an alternative embodiment for the formation of loops 236 with the various embodiments disclosed herein. According to this alternative embodiment, the loops 236 have one twist therein, such that they curve over each other to change the amount of spring force applied to the wall of the blood vessel.

Figure 57:
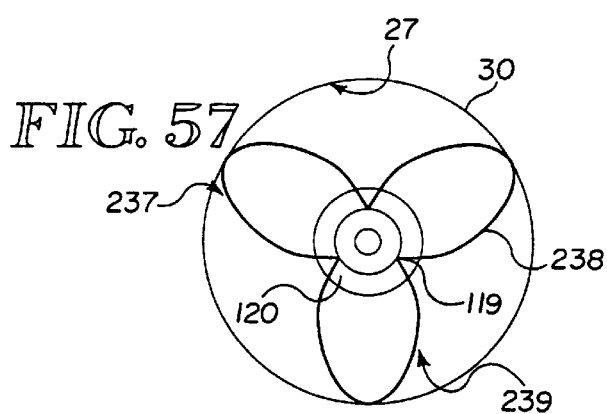

FIG. 57 illustrates an alternative embodiment in which three wire loops 237–239 are positioned equidistant from each other and extend from the surface 120 at a desired angle with respect to the end of the table for placement in the blood vessel. The wire to form the loops 237, 238 and 239 can be formed and implanted in a method similar to that taught for FIGS. 37 and 38. Alternatively, the wires can be attached to each other as taught by FIGS. 25–36, FIGS. 75–85 and the accompanying text. Specifically, one end of loop 238 can be attached to the other end of a loop 239 to form a common wire joint at 919.

Figure 58:
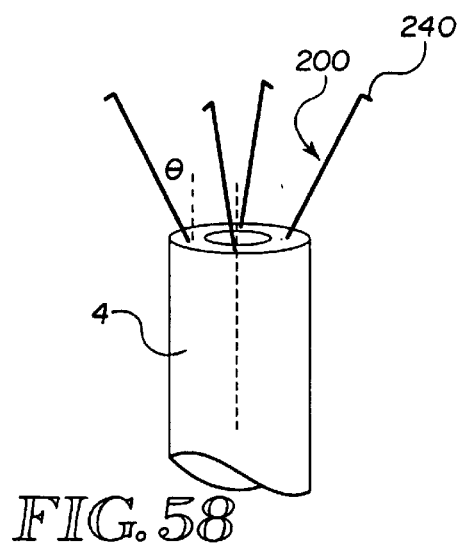

FIG. 58 illustrates an alternative embodiment in which the wire 200 has a vessel wire portion 240 bent at an angle of 90 degrees back towards the tubing 4. The angle of the bent portion 240 ensures that the vessel wire portion 240 will penetrate the blood vessel wall to the depth of the bend. Further, the wire 200 cannot be easily removed by retracting the tubing 4. Rather, the wires 200 must first be collapsed by one of the techniques previously described and then the catheter 4 can be removed.

Figures 59, 60:
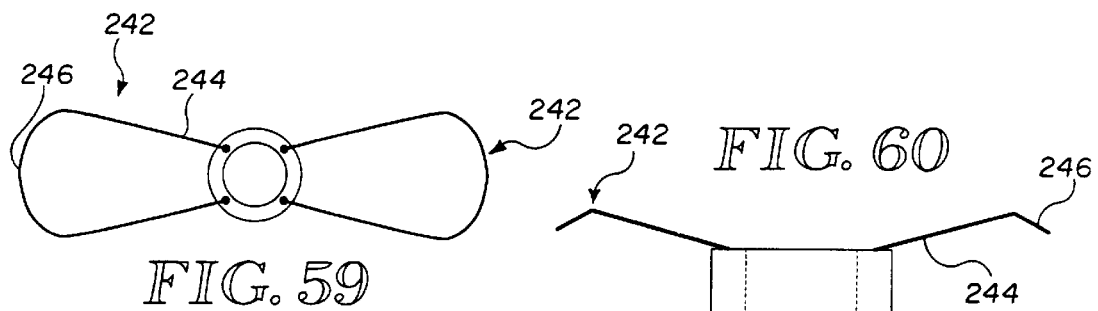

FIGS. 59 and 60 illustrate a further alternative embodiment of the tip retainer 9 according to the present invention. According to this alternative embodiment, loops 242 are formed from a wire in a manner previously described. As shown in FIG. 60, the loops 242 contain a straight portion 244 which extends at a. selected angle out of the distal end surface 120 of the tubing 4. The curved portions 246 of the loops 242 are bent downward at a desired angle, as shown in FIG. 60. The curved portion 246 contacts the side of the blood vessel wall to retain the catheter tube 4 in position within the blood vessel. In one example, the straight portion 244 is about 8 mm long for use in a blood vessel having a diameter less than about 30 mm.

Figures 61, 62:
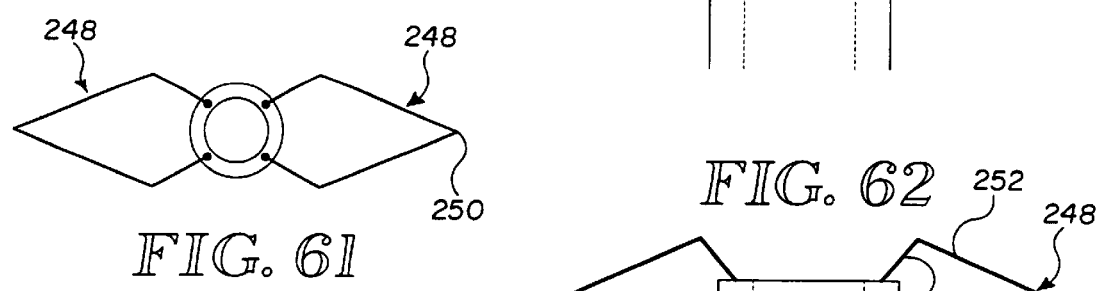

FIGS. 61 and 62 illustrate a further alternative embodiment for the tip retainer 9. According to this alternative embodiment, the loops 248 include a pointed tip area 250; a large, flat extending region 252; and a straight region 254. The loops 248 are generally in a diamond shape, extending in a straight wire portion and terminating in the tip 250. The tip 250 is generally sufficiently broad that it will not penetrate the wall of the blood vessel; however, it is sufficiently stiff that it will slightly indent the wall and firmly grip the side of the wall to anchor or secure the catheter tube 4 in the desired location.

Figures 63, 64:
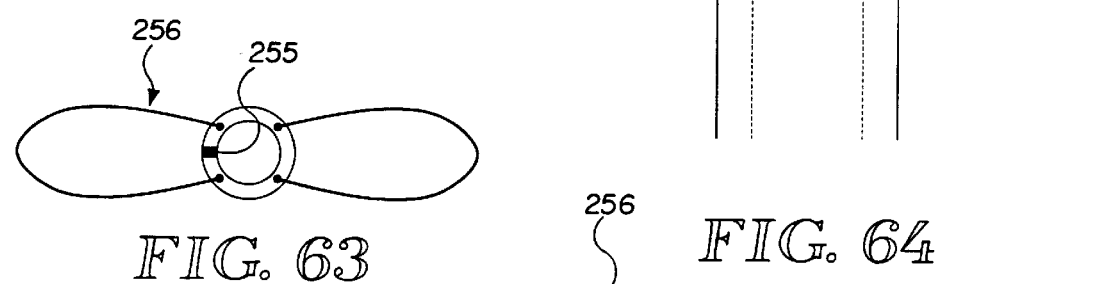
Figures 65, 66:
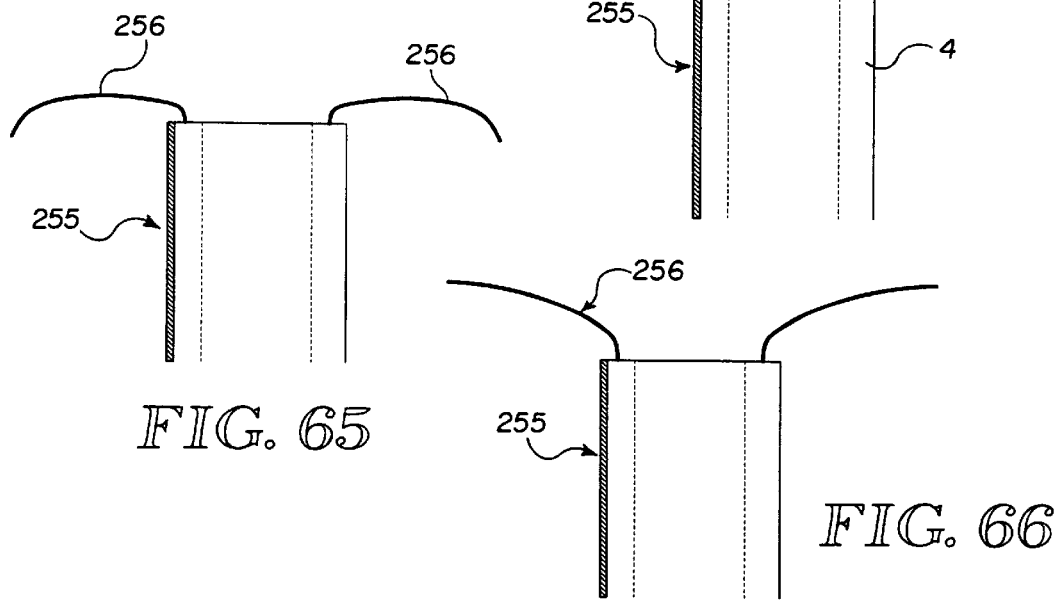

FIGS. 63–66 illustrate further alternative embodiments for the tip retaining member according to the present invention. According to the embodiment of FIG. 63, loops 256 are formed as generally curved loops. The portion of the wire 200 inserted into the catheter tube 4 is preferably at an angle of about 90-degrees with respect to the loop 256, as best shown in FIG. 64. The loops 256 may extend generally straight out from the wall of the tubing 4 and generally perpendicular thereto but include a rounded loop portion, as illustrated in FIG. 63. FIG. 65 illustrates a variation of this embodiment in which the loops 256 are slightly curved backwards, having the same gentle curve as shown in FIG. 63 but having a prestressed bend such that the end of the loop 256 is pointed slightly backwards, generally in the same direction as the catheter tube 4. FIG. 66 illustrates the embodiment in which the wires 256 are curved slightly upwards, with the ends generally perpendicular to the wall of the blood vessel, as shown. Each of the variations shown in FIGS. 63–66 include one or more radio opaque stripes 255 thereon to allow for the visualization of the relative position of the catheter in the insertion device and/or the blood vessel of the patient.

Figure 67:
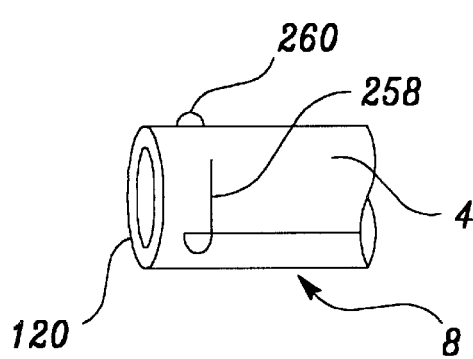
Figure 68:
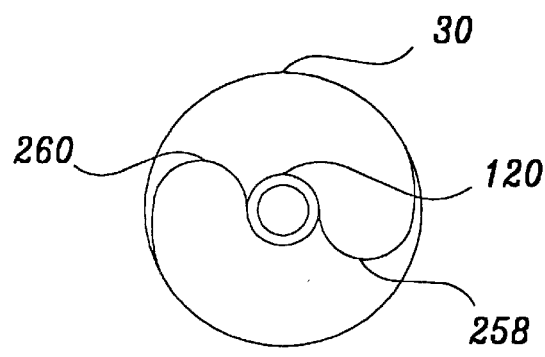
Figure 69:
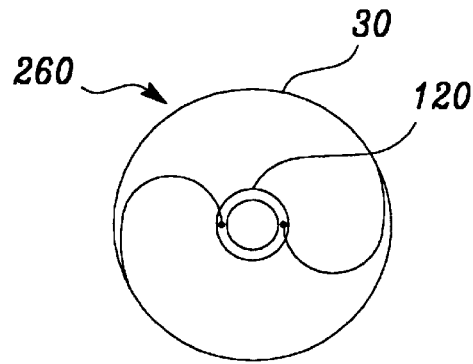

In the embodiment of FIGS. 67 and 68, the wires 258 and 260 are shown extending radially outwardly from the sidewall of the tip 8 and have a generally U-shaped orientation when viewed from the distal end of the catheter as shown in FIG. 68. With this configuration, lateral movement of the tip compresses the wires 258 and 260 to maintain the tip retainer 9 in position in the blood vessel 30. This embodiment may be placed in the blood vessel 30 using a sheath introducer or other member of the type generally shown in more detail in FIGS. 22–24 and explained herein. To ensure that the wires 258 and 260 are properly positioned in the blood vessel 30, the user may rotate the catheter clockwise in the blood vessel 30 once the sheath introducer or other member is removed from the blood vessel 30 to allow the ends of the wires 258 and 260 to rest against the wall of the blood vessel 30 generally perpendicular to the length of the catheter without penetrating the wall of the blood vessel. FIG. 69 illustrates the tip retainer 9 of FIG. 67 on the digital end surface 120 of the catheter 4.

Figure 70:
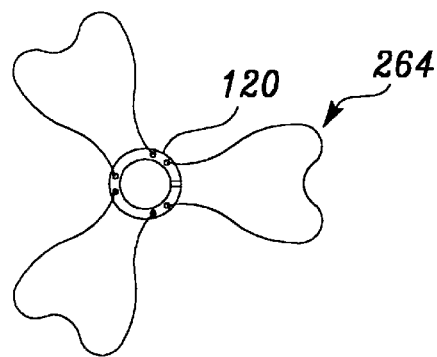
Figure 71:
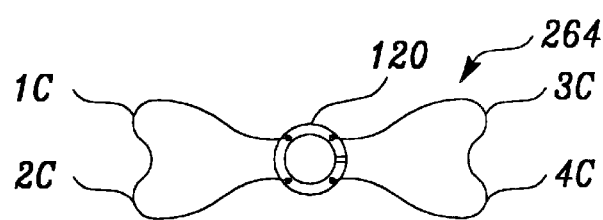

FIGS. 70 and 71 illustrate a cloverleaf design for loops 264. Each of the loops 264 is pre-bent into generally the shape of a single leaf of a cloverleaf, and thus each particular loop is assured to have at least two contact points with the wall of the blood vessel. For example, shown in FIG. 71, the minimum points of contact are labeled with the numerals 1c and 2c respectively for the left loop and 3c and 4c respectively for the right loop. FIG. 70 illustrates an embodiment in which three loops 264 are spaced equidistant around the tip portion 8 of the tube and FIG. 71 illustrates an embodiment in which only two loops are used. Both designs provide the advantage of multiple contact points assured for each of the loops 264 to increase the effectiveness of retaining the catheter tip within the blood vessel while permitting soft engagement with the blood vessel.

In one variation of the embodiments shown in FIGS. 70 and 71, the tips of the wires can be relatively thick and thus stiffer so that the tip itself retains the stiff shape, however, the central region between the contact points 1 and 2, as well as the base regions, can be a slightly more flexible wire (such as using the same wire but having a thinner cross-section) such that the bias force pressing the tip region outward for contact with the blood vessel is a relatively weak bias force with the tips extended in contact with the wall of the blood vessel. For the sake of clarity, the varied thickness of the wire of the loops 264 is not shown. If a single wire is used, it may gradually decreases in diameter with the smaller diameter portion towards the outer edge, then, as the wires depress further, it becomes stiffer and provides a stiffer spring bias force to resist the distal end portion 8 of the catheter 4 actually coming in contact with the wall. This design thus permits the tip portion 8 of the catheter relative movement within the blood vessel, but is effective in minimizing contact between the tip portion 8 and the blood vessel wall. Of course, a loop which has a differing stiffness along its length may be used with any one of the many embodiments described herein if desired. That is, any one of the many embodiments and alternative shapes for loops, as well as various other wires, may include wire which is stiffer in one portion of the wire than in another portion. The regions of relative stiffness and flexibility are selected with each design to permit slight relative movement of the tip catheter 8 within the blood vessel while being sufficiently stiff to prevent repeated contact between the distal end 8 of the catheter 4 and the blood vessel wall.

Figure 72:
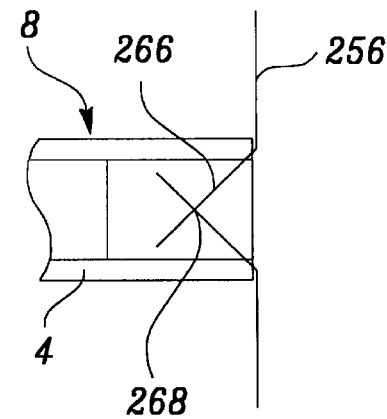
FIG. 72 illustrates an alternative embodiment for retaining the loops of the present invention in the tip portion of a catheter.

FIG. 72 illustrates an alternative embodiment for retaining the loops 256 in the tip portion 8 of the catheter 4. According to this alternative embodiment, the wire ends 266 are inserted into the catheter tube 4 at such an angle that they cross each other at a point 268. At the intersection 268, the wires can be affixed together by any suitable means, including glue, spotwelding, adhesive, twisting around each other, and the like. Inserting the wires 256 at a slant 266 to create an intersection 268 has been found to provide improved stability in the loops for maintaining the catheter 4 within the blood vessel and spaced from the wall.

Figure 74:
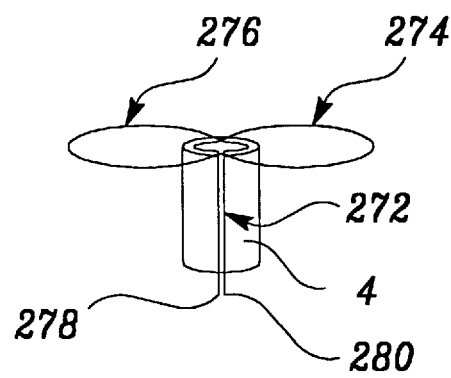
FIG. 74 is a perspective view of the embodiment shown in FIG. 73.

FIGS. 73 and 74 illustrate further alternative embodiment, modifications of which are also shown in FIGS. 75–81.

An explanation of some of the difficulties encountered in actual in vivo testing may be helpful in understanding the further alternative embodiments. One difficulty which has been encountered with some embodiments is that the loops may twist, or overlap each other. The blood vessel of a living animal is subject to frequent movement, pulsation, and sometimes trauma, depending upon the activity being undertaken. As a result, the wires loops may sometimes become displaced, occasionally twisting on top of each other. Stiffer wire has been found in some instances to be helpful to prevent the twisting action in some catheters. This may overcome the problem; however, this may increase the trauma to the blood vessel and some twisting may still occur. Therefore, the wire may have to have a stiffness in excess of that desired for the spring action in the blood vessel in order to prevent the loops from rotating over each other.

Figure 75:
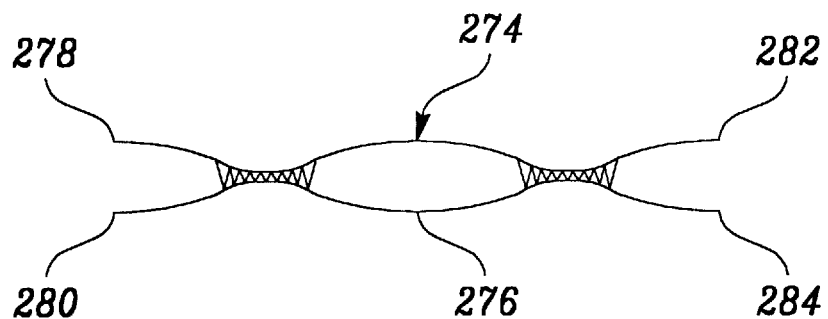
FIG. 75 is a side view of the wire used in the embodiment shown in FIG. 73.

The alternative embodiments of FIGS. 73–81 are various approaches to solve the twisting problem that may occur in other models. According to the embodiment shown in FIGS. 73 and 74, the wires may be inserted together down the same guideway. Four wires ends are used, two for each wire of the two loops, but only two guideways, 270 and 272, are used. In this embodiment, loop 274 is formed from the wire that has ends 278 and 282 and loop 276 is formed from the wire that has ends 280 and 284. End 278 of loop 274 and end 280 of loop 276 are placed together as shown in FIG. 75. While being held together, both are inserted and secured into the single guideway 272 in the end of the catheter 4. Similarly, ends 282 and 284 of loops 274 and 276, respectively, are held together and inserted into the single guideway 270. If desired, Teflon™ or appropriate coating is placed on the exposed portions of the wire. The embodiments of FIGS. 73 and 74 provide better loop stability than some of the previous models.

Figure 76:
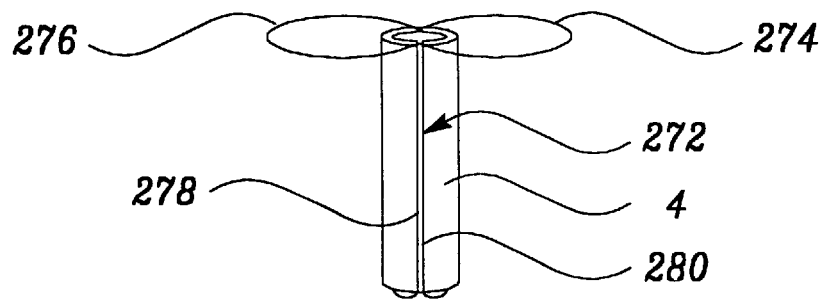
FIG. 76 is a view similar to the view shown in FIG. 74 with the twisted wire positioned closer to the distal end of the catheter than in FIG. 74.
Figure 77:
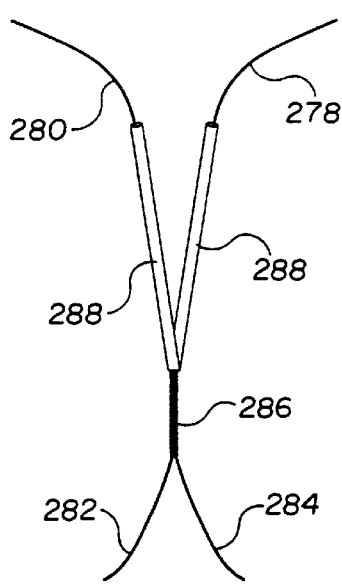
FIGS. 77–81 are illustrative of further variations of the alternate embodiment shown in FIG. 73.

FIGS. 75 and 76 further illustrate the embodiment of FIGS. 73 and 74 for providing increased stability of the loops. According to this embodiment, the wire that forms the loop 274 is twisted at end 278 with the wire that forms loop 276 at its respective end 280. The wires are firmly twisted together, intertwining them and interlocking them with each other. The wire which actually makes the loops 274 and 276 is left untwisted, the length of the untwisted portion being selected based on the desired size of the loops, which may vary over ranges previously described, for example, from about 15 mm or less up to about 30–40 mm or more, depending on the size of the blood vessel and the intended loop configuration. The other ends of 282 and 284 are then twisted together as shown in FIG. 75, firmly retaining the wires together at this end. The respective ends 278, 280, 282, and 284 are then cut short to the desired length.

Alternatively, as described in more detail herein, the wires may have sufficient length to extend along the entire length of the catheter tube 4 and exit at the proximal end for control by an operator.

After the ends of the wires are joined together, they are inserted into the guideway lumens 270 and 272 as previously described and shown in FIG. 73 and 74. The ends of the wires are secured into the end of the catheter tubing 4. This design provides increased loop stability over the previous models and FIG. 76 is illustrative that the side of the loops 274 and 276 may be further adjusted by moving the area of the twisted wire distally or proximally in the guideway.

Figure 78:
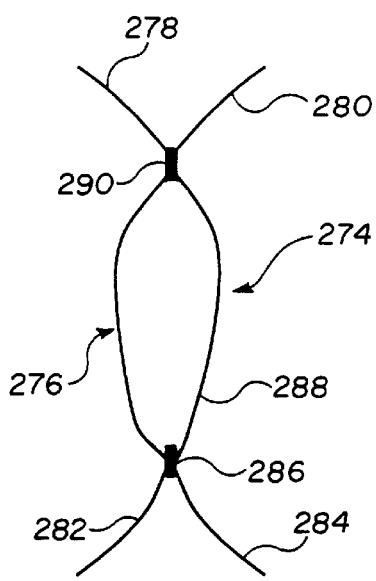
Figure 79:
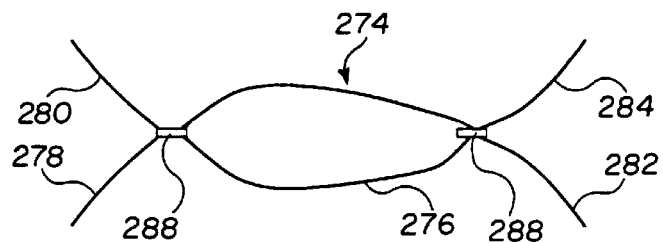
Figure 81:
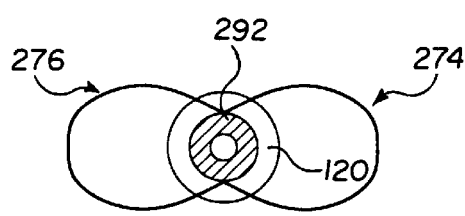

FIGS. 77–81 illustrate further variations of the embodiment of FIGS. 73–76. According to this variation, two stainless steel wires of a desired length are selected to form the loops 274 and 276. The wires are welded together at spotweld 286 to retaining the loops at a fixed position with respect to each other. The welding may be any desired technique for solidly affixing the two wires to each other to prevent lateral and rotational movement with respect to each other at the weld. For example, spotwelding using a conventionally available spotwelder having a weld distance in the range of 3 to 5 mm has been found acceptable for the spotweld 286. Alternatively, solder has been found to be an acceptable technique for affixing the wires to each other, similar to that done in a weld. In the embodiment shown in FIGS. 77–81, heat shrink tubing 288 is placed over the wires which will form the loops 274 and 276. These loops will come in contact with the wall of the blood vessel and the heat shrink Teflon™ tubing minimizes the likelihood of adverse reactions in the body of the patient. After the tubing 288 is in position, ends 278 and 280 are welded together at spot 290 using the technique previously described with respect to the spotweld 286. In one embodiment, the wires cross each other at the intersection, each wire being slightly bowed with the ends extending in opposite directions from that of the loop, shown with loop 274 having ends 278 and 282 extending on the other side of the weld, as best seen in FIG. 78. Alternatively, in one embodiment, the wires are positioned side by side so they both extend juxtaposed with respect to each other and are welded.

Figure 80:
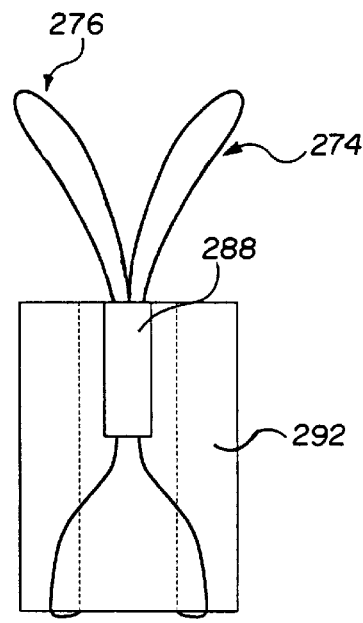

After ends 286 and 290 are welded together, tubing 288 may be placed over the welds 286 and 290. The assembly is then subjected to heat treatment to heat shrink the tubing into a tight position completely covering the welds and guarding against the possibility of the welds coming in contact with the body or the blood vessel. The ends 278, 280, 282, and 284 may then be formed into hooks and cut to the appropriate length for insertion into the catheter tube 4. According to the embodiment shown in FIG. 81, the hooks are inserted around the cylinder 292 in a manner similar to that shown in FIG. 38 with small cylinder 97. The welded points 286 and 290 are on opposite sides of the cylinder 292, spaced from each other so that the loops 274 and 276 may be appropriately formed. The tubing 292 is then inserted into the lumen of the catheter tubing 4, firmly retaining the welded areas 286 and 290 within the catheter 4. This is similar to the technique previously described with respect to FIG. 38, except that the wires are welded together and they extend down to the bottom of the insertion tube to hook around the bottom of the cylinder 292 as shown in FIG. 80. The loops 274 and 276 are then formed in the desired shape. An adhesive may also be injected between the inner diameter of the tube 4 and the outer diameter of cylinder 292 to help secure cylinder 292 within tube 4. Such an adhesive may also be used on other of the embodiments herein, as needed.

According to an alternative embodiment, and preferred in many applications, the two ends of the wires at the welded junctions 286 and 290 are inserted into respective lumens 270 and 272 within the catheter 4. The joined wires are inserted into the guideways so that the joined regions, whether soldered or welded, are just inside the guideways. The ends of the wires extend through the guideways for manipulation by a physician, or are further welded or otherwise joined into a single wire so that the single wire may be manipulated by a physician, as explained in more detail above.

The wires constructed according to the embodiments of FIGS. 76–81 have shown a significantly increased stability and resistance to twisting. The loops are stabilized and do not rotate over each other. According to current designs, the closer the wires are joined together towards the catheter tip, the greater the stability of the loops. The increased stability makes it more difficult for the loops to twist over each other and become tangled. This technique also permits wires of a desired spring constant or resistance having a desired stiffness to be used and yet maintain the stability of the loops within the blood vessel. That is, the technique of using stiffer wire for the loops to maintain them in position may be replaced by the joint welding technique so that wires having less overall stiffness can be used and having the desired spring constant or resistance to spring against opposing wall sections of the blood vessel while maintaining the distal end of the catheter a variable but spaced apart distance from the wall of the blood vessel.

One further advantage of the use of various curved loops, such as the embodiments shown in FIGS. 59–81, is that the loops may be formed with a gentle arc therein. The wire curves in an arc, such as shown in FIG. 65. FIG. 60 shows a more rigid configuration. The arc of the wire provides an additional spring tension region between the vessel wall and the catheter 4. This spring tension is extremely helpful in minimizing the damage caused by the loop in contact with the vessel wall. That is, as the catheter is moved back and forth with the pulsations of the blood, the spring tension in the arc region of the loop acts to absorb some of the shock to permit slight movement of the catheter, and yet, as the catheter 4 becomes closer to the wall, the spring tension of the loop increases to push the catheter back towards the central region of the vessel, preventing, or at least minimizing, direct contact with the vessel wall. A similar arc may also be used in any of the other loop embodiments described herein to provide these advantages.

Figure 82:
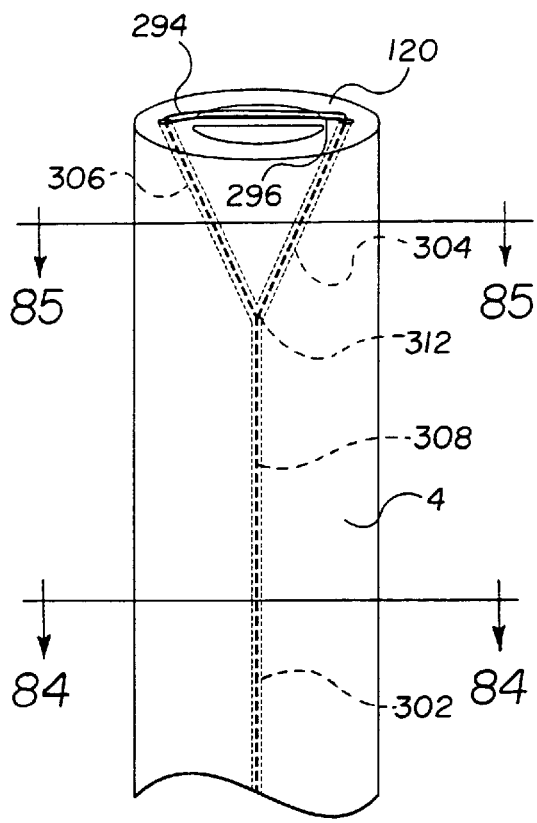
FIG. 82 is a side view of a double lumen catheter having a guideway extending the length of the catheter.
Figure 83:
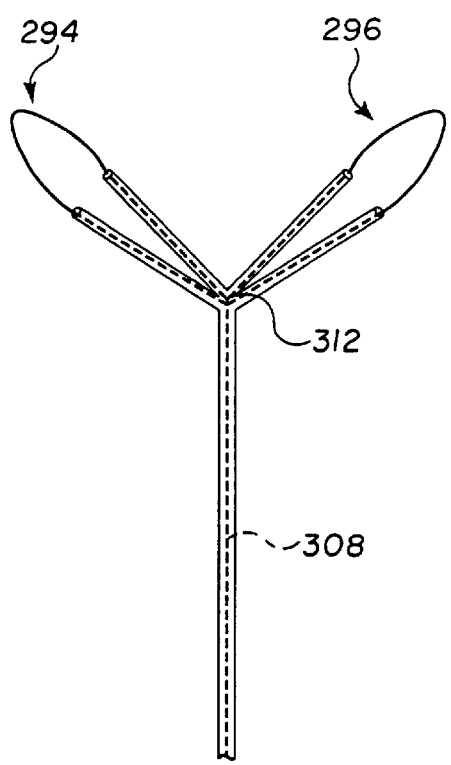
FIG. 83 is a side view of the tip retainer assembly outside of the catheter for use in the various embodiment of prior figures, such as that shown in FIGS. 7–9, 37, 38, 56, 57, 59, 63, 82, etc.
Figure 84:
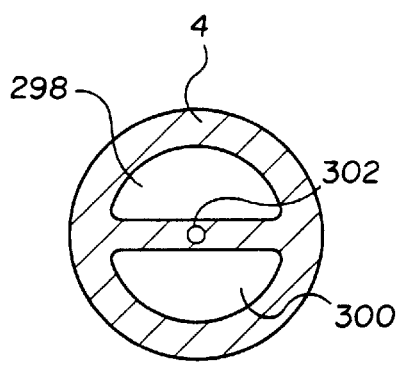
FIGS. 84 and 85 are cross-sectional views of the embodiment shown in FIG. 82 taken at the locations indicated in FIG. 82.
Figure 85:
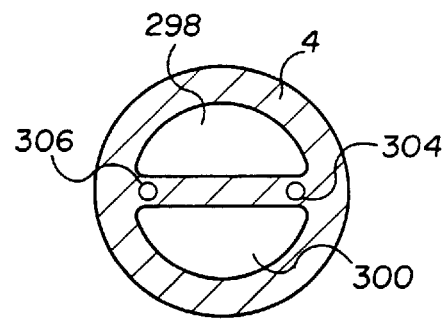

FIGS. 82–85 illustrate a further alternative embodiment manufactured according to principles of the present invention. As best shown in FIGS. 84 and 85, the catheter 4 includes two lumens, 298 and 300, respectively. The catheter is of the standard double-D type, or alternatively, of the same type as shown in FIG. 3, having two separate lumens 42 and 44 and a wall separating the lumens.

According to the embodiment shown in FIGS. 82–85, a guideway 302 is provided within the wall separating the lumens 298 and 300. The guideway 302 extends along the entire length of the catheter 4 so that a wire placed therein may exit at the proximal end for manipulation by a physician. The guideway 302 continues as a single channel until it reaches the distal end 8 of the catheter, just prior to the distal end surface 120. In the distal end 8, the guideway 302 branches into two guideways, 304 and 306, respectively as shown in FIG. 85. The wire exits from the guideways 304 and 306 forming loops 294 and 296. The loops 294 and 296 are formed in a manner similar to that previously described with respect to FIGS. 76–81. Namely, one end of the wire that forms the loop 294 exits from the same lumen 304 as one end of the wire that forms loop 296. Similarly, the other ends of loops 294 and 296 exit from the same lumen 306. The lumen is preferably Teflon™-lined to provide a low friction surface to permit the loops 294 and 296 to be deployed and retracted as necessary.

The wire 308, as best shown in FIG. 83, can be constructed according to alternative embodiments. According to one embodiment, the wire 308 is a twisted bundle of four wires, extending from the respective ends of loops 294 and 296. Preferably, the bundle of wires are spotwelded at the two respective junctions just prior to exiting from the respective guideways 304 and 306 as previously described with respect to FIGS. 77–81. (FIG. 83 shows the two loops 294 and 296 prior to the spot welding at the two respective junctions at the exit from-guideways 304 and 306; if it is to be used in the catheter of FIG. 82. The two pairs of wires are then again spotwelded together at junction 312, forming a common branch area for the four wires. The four wires may then be twisted together or appropriately formed in a bundle to form effectively a common wire 308 extending the length of the guideway and exiting at the posterior end for manipulation by the physician.

According to a further alternative embodiment, the wire 308 may be a single strand of steel wire, extending as a single strand along the entire length of the guideway 302 to a branch area or position 312 within the guideway as shown in the drawings. At the branch position 312, the single wire 308 may have two separate wires welded to the end thereof to form the two loops 294 and 296, respectively. Both ends of the two wires 294 and 296 are welded to the end of the common wire 308 and the wires are preferably appropriately welded to each other as previously described to provide stable loops 294 and 296 having the desired spring or resiliency.

Having a single wire 308 that extends the length of the catheter 4 provides certain advantages over some of the techniques described above. Frequently, the catheter 4 undergoes series of bends and curves along its length when it is positioned within the blood vessel. Of course, the catheter may bend and curve as it is inserted into the blood vessel and may, in some embodiments when finally at rest, be relatively straight. Alternatively, the catheter may pass through a bend in the blood vessel so that the catheter undergoes a,significant bend and remains in the bent position when the distal end 8 of the catheter is in the desired position for deployment of the tip retainer 9. When the catheter tube 4 is bent, wires that are at different locations along the longitudinal axis of the catheter tube 4 will undergo different changes in length. For example, a wire along the outside diameter of a bend must travel a longer path and the wire or loop on the distal end of the catheter end will be correspondingly shortened as compared to the remaining loops or wires on the distal end of the catheter. On the other hand, a wire on an inside surface of a bend travels a shorter path with a result in effect that the wire or loop will be extended further from the distal end of the catheter than the remaining loops or wires on the distal end of the catheter. Unfortunately, the bends in the wire on the distal end of the catheter may distort the size and shape of the loops in the tip retainer 9 as it is inserted within the body. Use of a single wire 308 avoids these problems. Specifically, the wire 308 may undergo a series of bends and curves which may change the length of travel of the wire in the guideways of the catheter. This change in the length of extension of the respective wires or loops analogous to two cars traveling side by side along a race track. The car on the inside travels a shorter distance than the car on the outside on a curve. The effect of the different lengths of travel can become a factor for the proper placement of the catheter because minor differences, such as, about 1 mm may cause the catheter to be off center or contact the wall of the blood vessel.

However, in the present embodiment, all of the wires or loops which entered from the distal end of the catheter are connected to the single wire 308 and, thus, all the wires will be similarly effected by the bending or curvature of the catheter. In the embodiment of FIGS. 82 and 84, the wire 308 extends through a central lumen 302 between two lumens. This guideway 302 is aligned with the longitudinal axis of the catheter 4. Thus, even if the four wires are not tied together and each extends individually along the guideway 302, none of them will be lengthened or shortened with respect to the distal end of the catheter because they all extend in line with the longitudinal axis of the catheter. However, it is not necessary to have all of the wires extend along the longitudinal axis of the catheter in order to obtain the advantages of having all the wires extend down a single lumen. Even if the lumen is along a sidewall, if all of the wires are in the same guideway, any change in length which is caused by a bend or curve in the catheter 4 will cause an identical change in all of the wires because they are all within a single guideway. Thus, even if the actual position and length of the loops may change, their relative positions remain the same and the loops may be properly deployed to retain the catheter 4 within the central region of the blood vessel, and spaced from the walls thereof.

Another advantage of this embodiment is that the wire 308 can have a different spring constant or resiliency and strength than the wires that form the loops 294 and 296. For example, a stiff or rigid cable for 308 may be selected, having the desired properties for extending, retracting, and control such as a braid steel or solid cable. Wire 308 does not directly contact the body and therefore may be constructed of stiffer wire with less concern for the body interaction or injury. Wires for loops 294 and 296, as well as the similar wires of embodiments shown in FIGS. 25–35 and 71–81, are preferably made of a different material which preferably has the desired spring tension properties as previously described and may be preferably coated so as not to cause a reaction in the body. These wires or loops may also be formed of a material that is selected with less concern for the rigidity or stiffness properties that would be required of a wire if it were also used for retraction and extension such as wire 308. Use of different material for wire 308 and loops 294 and 296 or for parts thereof, allow for the optimum operation of each for their particular environment, and therefore provide a distinct advantage over a single wire which must satisfy potentially conflicting criteria. The structure and advantages obtained thereby of wire 308 may also be adopted in the design of wire 172, and vice versa, as desired.

The wire shown in the various embodiments described herein is a wire having the desired dimensions and spring properties shown in the drawings. According to one alternative embodiment, a memory wire could be used to construct the loops for any of the embodiments described herein. The memory wire is a wire which is known on the open market but has yet to be used within the environment of that discussed for the present invention. Memory wire is the type of wire which can assume different shapes depending upon the temperature. When the wire reaches a certain temperature or above, the wire assumes a predetermined shape into which it has been previously formed. When the wire is below the selected temperature, the wires preferably do not retain their desired installed or predetermined shape.

In the embodiment in which a memory wire is used, the wires may be more easily positioned within the introducer sheath or, wrapped around the end of catheter. Alternatively, the ends of the wires may actually be placed inside the lumen of the catheter 4 so that the catheter 4 may be introduced into the patient with a minimum cross-sectional area. Once the wires are inside the body of the animal, they will slowly begin to heat up. During the warm-up period, the catheter 4 may be worked with and positioned to place the tip 8 at a desired location. As previously mentioned, a fluoroscope, ultrasonic imaging or other technique may be used to exactly locate tip 8 within the blood vessel. After a selected period of time, depending on the type of memory wire used but preferably a few moments after being. positioned within the blood stream, the memory wires will begin to heat up and the loops begin to be deployed. As the memory wire increases in temperature to reach the selected temperature at which they assume the preselected shape, the loops are deployed and spring outward to contact the walls of the blood vessel and center the catheter 4 within the blood vessel in the manner which has been previously described. The use of memory wire for the loops provide significant advantages in the ease of insertion and positioning of tip 8.

While the preferred embodiments of the invention have been illustrated and described, it will be appreciated that various changes can be made therein without departing from the spirit and scope of the invention as defined in the following claims.

We claim:

1. A catheter adapted for insertion into a blood vessel having blood flowing therethrough, comprising:

an elongated tubular member having an internal first lumen for permitting fluids to pass through the catheter and having distal and proximal end portions thereon and a second lumen, said first lumen having a first diameter and said second lumen having a second diameter therein;

a resilient tip immobilizing means at said distal end portion of said tubular member for anchoring said distal end portion of said tubular member within the blood flow of the blood vessel to maintain said distal end portion of said tubular member in a resilient spaced relationship from the blood vessel wall and prevent the distal end portion of said tubular member from contacting a wall of the blood vessel without substantially obstructing fluid flow of blood through the blood vessel, such that catheter failure due to stenosis at said distal end portion of said tubular member is reduced;

a single cable member in contacting engagement with said tip immobilizing means and extending along said second lumen having a second diameter wherein said first diameter of said first lumen is greater than said second diameter of said second lumen and wherein said second lumen extends from said proximal end portion to said distal end portion of said tubular member to actuate movement of said tip immobilizing means upon movement of said cable member in said second lumen; and said tip immobilizing means includes a plurality of loop members extending from said cable member.

2. The catheter according to claim 1 wherein said plurality of loop members each include a base region thereon and being connected at said base region to another of said plurality of loop members at said base region thereof, said plurality of loop members having base regions that are connected together to provide a stabilized relationship between said loop members.

3. The catheter according to claim 1 wherein said loop members are fixedly connected to each other to prevent rotational movement of said loop members with respect to each other.

4. The catheter according to claim 1 in which each of said loop members has two base regions with one base region from each loop member being connected to a base region in common with each of the other loop members.

5. The catheter according to claim 1 wherein each of said loop members has base regions and said loop members are connected to each other and said cable member.

6. A catheter adapted for insertion into a blood vessel having blood flowing therethrough, comprising:

an elongated tubular member having an internal first lumen for permitting fluids to pass through the catheter and having distal and proximal end portions thereon and a second lumen, said first lumen having a first diameter and said second lumen having a second diameter therein;

a resilient tip immobilizing means at said distal end portion of said tubular member for anchoring said distal end portion of said tubular member within the blood flow of the blood vessel to maintain said distal end portion of said tubular member in a resilient spaced relationship from the blood vessel wall and prevent the distal end portion of said tubular member from contacting a wall of the blood vessel without substantially obstructing fluid flow of blood through the blood vessel, such that catheter failure due to stenosis at said distal end portion of said tubular member is reduced;

a single cable member in contacting engagement with said tip immobilizing means and extending along said second lumen having a second diameter wherein said first diameter of said first lumen is greater than said second diameter of said second lumen and wherein said second lumen extends from said proximal end portion to said distal end portion of said tubular member to actuate movement of said tip immobilizing means upon movement of said cable member in said second lumen; and wherein said tip immobilizing means includes at least one loop member thereon and said single cable member is connected to a base region of said at least one loop member with said single cable member extending in said second lumen from a distal end portion thereof to a proximal end portion thereof.

7. A catheter for insertion into a target organ or blood vessel of a patient, comprising:

an elongate catheter body having distal and proximal end portions with a hub member positioned thereon and wherein said hub member may be rotated with respect to said catheter body and said catheter body further including a first passageway with a first diameter in said catheter body for permitting the flow of fluids through said first passageway and a second passageway with a second diameter therein; and a resilient tip restraining member including at least one loop member extending and operatively located along said distal end portion of said catheter body and in movable communication with said hub member via said second passageway in said catheter body wherein said first diameter of said first passageway is greater than said second diameter of said second passageway and said tip restraining member is movable in response to rotational movement of said hub member with respect to said catheter body between a first retracted position and a second extended position for securing said distal end portion of said catheter body in a resilient spaced apart relationship from the tissue of the target organ or blood vessel of the patient and inhibiting the contact between said distal end portion and the target tissue or blood vessel of the patient while allowing the flow of fluids therethrough and therearound and reducing catheter obstruction or failure.

8. A catheter for insertion into a target organ or blood vessel of a patient, comprising:

an elongate catheter body having distal and proximal end portions with a hub member operatively positioned thereon and a first passageway with a first diameter in said catheter body for permitting the flow of fluids through said first passageway and a second passageway with a second diameter therein; and a resilient tip restraining member including at least one loop member extending and operatively located along said distal end portion of said catheter body and in movable communication with said hub member via said second passageway in said catheter body wherein said first diameter of said first passageway is greater than said second diameter of said second passageway and said tip restraining member is movable between a first retracted position and a second extended position for securing said distal end portion of said catheter body in a resilient spaced apart relationship from the tissue of the target organ or blood vessel of the patient and inhibiting the contact between said distal end portion and the target tissue or blood vessel of the patient while allowing the flow of fluids therethrough and therearound and reducing catheter obstruction or failure; and wherein said catheter body includes a single cable member connected between said hub member and said at least one loop member to enable the movement of said at least one loop member between said first and second positions.

9. A catheter for insertion into a target organ or blood vessel of a patient, comprising:

an elongate catheter body having distal and proximal end portions with a hub member operatively positioned thereon and a first passageway with a first diameter in said catheter body for permitting the flow of fluids through said first passageway and a second passageway with a second diameter therein; and a resilient tip restraining member operatively located along said distal end portion of said catheter body and in movable communication with said hub member via said second passageway in said catheter body wherein said first diameter of said first passageway is greater than said second diameter of said second passageway and said tip restraining member is movable between a first retracted position and a second extended position for securing said distal end portion of said catheter body in a resilient spaced apart relationship from the tissue of the target organ or blood vessel of the patient and inhibiting the contact between said distal end portion and the target tissue or blood vessel of the patient while allowing the flow of fluids therethrough and therearound and reducing catheter obstruction or failure; and wherein said tip restraining member includes a plurality of loop members each of which extend from said distal end portion of said catheter body in said second position and are adjacent to said catheter body in said first position.

10. The apparatus according to claim 9 wherein said plurality of loop members are connected to a common location along the distal end portion of the catheter body to resiliently contact the wall of the blood vessel to maintain a spaced apart relationship therebetween in said second position of said tip restraining member.

11. A catheter for insertion into a target organ or blood vessel of a patient, comprising:

an elongate catheter body having distal and proximal end portions with a hub member operatively positioned thereon and a first passageway with a first diameter in said catheter body for permitting the flow of fluids through said first passageway and a second passageway with a second diameter therein; and a resilient tip restraining member operatively located along said distal end portion of said catheter body and in movable communication with said hub member via said second passageway in said catheter body wherein said first diameter of said first passageway is greater than said second diameter of said second passageway and said tip restraining member is movable between a first retracted position and a second extended position for securing said distal end portion of said catheter body in a resilient spaced apart relationship from the tissue of the target organ or blood vessel of the patient and inhibiting the contact between said distal end portion and the target tissue or blood vessel of the patient while allowing the flow of fluids therethrough and therearound and reducing catheter obstruction or failure; and wherein said tip restraining member includes a distal end portion consisting of a plurality of wires thereon and wherein said wires include a coating thereon to reduce the adherence of blood thereto.

12. The apparatus according to claim 11 wherein said second passageway includes a cable member extending therethrough and said hub member is connected to said cable member and actuates said cable member in said catheter body to move said cable member with respect to said catheter body in response to movement of said hub member to extend and retract said tip restraining member from said distal end portion of said catheter body.

13. The apparatus according to claim 12 wherein rotation of said hub member causes said tip restraining member to move between first and second positions such that said tip restraining member is in said first position during insertion of said catheter body into the target organ or blood vessel of the patient and is movable to said second position upon rotation of said hub member.

14. A method for reducing catheter failure due to stenosis or thrombosis at a catheter tip using a catheter having distal and proximal end portions, a hub member and a positioning member having at least one loop member thereon, the method comprising:

(a) placing the catheter and positioning member within a blood vessel such that the distal end portion of the catheter is positioned at a predetermined location within the blood vessel;

(b) deploying the at least one loop member from a first position wherein the at least one loop member is retracted to a second position wherein the at least one loop member is deployed by rotating the hub member such that the at least one loop member extends radially outward from the catheter into resilient contact with a wall of the blood vessel for securing a portion of the catheter within the blood vessel to maintain the secured portion of the catheter in a resilient spaced apart relationship from the wall of the blood vessel without substantially obstructing fluid flow through the blood vessel in the second position; and (c) retracting the at least one loop member from the second position to the first position by rotating the hub member for removal of the catheter from the blood vessel of the patient.

15. The method of claim 14 wherein the at least one loop member is retracted with respect to the secured portion of the catheter prior to removal of the catheter from the blood vessel by actuating the hub member which is positioned along the proximal end portion of the catheter and is connected to a cable member such that actuation of the hub member actuates movement of the cable member which is positioned along the lengthwise dimension of the catheter and which causes retraction of the at least one loop member.

16. The method of claim 14 wherein rotation of the hub member in a first direction causes deployment of the at least one loop member to the second position, and the rotation of the hub member in a second direction causes the retraction of the at least one loop member from the second position of the at least one loop member of the catheter.

* * * * *